US011464966B2

(12) United States Patent
Gross et al.

(10) Patent No.: US 11,464,966 B2
(45) Date of Patent: Oct. 11, 2022

(54) DELIVERY OF IMPLANTABLE NEUROSTIMULATORS

(71) Applicant: BLUEWIND MEDICAL LTD., Herzliya (IL)

(72) Inventors: Yossi Gross, Moshav Mazor (IL); Gur Oron, Tel Aviv (IL); Bar Eytan, Gedera (IL); Zev Sohn, Ginot Shomron (IL)

(73) Assignee: BLUEWIND MEDICAL LTD., Herzlia (IL)

( * ) Notice: Subject to any disclaimer, the term of this patent is extended or adjusted under 35 U.S.C. 154(b) by 0 days.

(21) Appl. No.: 17/410,514

(22) Filed: Aug. 24, 2021

(65) Prior Publication Data

US 2021/0379366 A1    Dec. 9, 2021

Related U.S. Application Data

(63) Continuation of application No. 16/363,256, filed on Mar. 25, 2019, now Pat. No. 1,128,719, which is a continuation of application No. 15/860,385, filed on Jan. 2, 2018, now Pat. No. 10,238,863, which is a continuation of application No. 14/649,873, filed as
(Continued)

(51) Int. Cl.
| | | |
|---|---|---|
| *A61N 1/05* | (2006.01) | |
| *A61N 1/36* | (2006.01) | |
| *A61N 1/372* | (2006.01) | |

(52) U.S. Cl.
CPC ......... *A61N 1/0558* (2013.01); *A61N 1/0551* (2013.01); *A61N 1/0556* (2013.01); *A61N 1/36017* (2013.01); *A61N 1/37205* (2013.01)

(58) Field of Classification Search
CPC .. A61N 1/0558; A61N 1/0551; A61N 1/0556; A61N 1/36017; A61N 1/37205
See application file for complete search history.

(56) References Cited

U.S. PATENT DOCUMENTS

| | | |
|---|---|---|
| 3,411,507 A | 4/1964 | Wingrove |
| 3,693,625 A | 9/1972 | Auphan |
| | (Continued) | |

FOREIGN PATENT DOCUMENTS

| | | |
|---|---|---|
| DE | 102008054403 | 6/2010 |
| EP | 0 688 577 | 12/1995 |
| | (Continued) | |

OTHER PUBLICATIONS

An Office Action dated Apr. 22, 2019, which issued during the prosecution of U.S. Appl. No. 15/638,924.
(Continued)

*Primary Examiner* — Amanda K Hulbert
*Assistant Examiner* — Natasha Patel
(74) *Attorney, Agent, or Firm* — Sughrue Mion, PLLC

(57) ABSTRACT

An implant that includes an electrode is advanced to a nerve of a subject using a tube. The tube and the implant are arranged at a nonzero angle with respect to a skin surface of the subject, and the implant is passed distally from an opening of the tube, in a vicinity of a portion of the nerve. A longitudinal axis of the implant is realigned to become generally parallel with the skin surface, by proximally withdrawing the tube from the subject. Other embodiments are also described.

10 Claims, 20 Drawing Sheets

Related U.S. Application Data application No. PCT/IB2013/060607 on Dec. 3, 2013, now Pat. No. 9,861,812.

(60) Provisional application No. 61/733,995, filed on Dec. 6, 2012.

(56) References Cited

U.S. PATENT DOCUMENTS

| | | |
|---|---|---|
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lau |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,036,854 A | 8/1991 | Schollmeyer et al. |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr |
| 5,344,439 A | 9/1994 | Otten |
| 5,411,535 A | 5/1995 | Fujii et al. |
| 5,423,872 A | 6/1995 | Cigaina |
| 5,439,938 A | 8/1995 | Synder et al. |
| 5,454,840 A | 10/1995 | Krakovsky et al. |
| 5,487,760 A | 1/1996 | Villafana |
| 5,505,201 A | 4/1996 | Grill, Jr |
| 5,540,730 A | 7/1996 | Terry, Jr |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Fei et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,071,274 A | 6/2000 | Thompson et al. |
| 6,091,992 A | 6/2000 | Bourgeois |
| 6,083,249 A | 7/2000 | Familoni |
| 6,086,525 A | 7/2000 | Davey et al. |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Schwartz |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,496,729 B2 | 12/2002 | Thompson |
| 6,496,730 B1 | 12/2002 | Kleckner et al. |
| 6,582,441 B1 | 6/2003 | He et al. |
| 6,591,139 B2 | 7/2003 | Loftin et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,712,772 B2 | 3/2004 | Cohen et al. |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,770,022 B2 | 8/2004 | Mechlenburg |
| 6,788,973 B2 | 9/2004 | Davis et al. |
| 6,788,975 B1 | 9/2004 | Whitehurst et al. |
| 6,804,561 B2 | 10/2004 | Stover |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 6,950,706 B2 | 9/2005 | Rodriguez et al. |
| 6,993,384 B2 | 1/2006 | Bradley et al. |
| 7,015,769 B2 | 3/2006 | Schulman et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,054,689 B1 | 5/2006 | Whitehurst et al. |
| 7,054,692 B1 | 5/2006 | Whitehurst et al. |

(56) References Cited

U.S. PATENT DOCUMENTS

| | | |
|---|---|---|
| 7,110,820 B2 | 9/2006 | Tcheng et al. |
| 7,149,575 B2 | 12/2006 | Ostroff et al. |
| 7,151,914 B2 | 12/2006 | Brewer |
| 7,174,218 B1 | 2/2007 | Kuzma |
| 7,177,690 B2 | 2/2007 | Woods et al. |
| 7,177,698 B2 | 2/2007 | Klosterman et al. |
| 7,190,998 B2 | 3/2007 | Shalev et al. |
| 7,203,549 B2 | 4/2007 | Schommer et al. |
| 7,209,792 B1 | 4/2007 | Parramon et al. |
| 7,212,867 B2 | 5/2007 | Venrooij et al. |
| 7,216,000 B2 | 5/2007 | Sieracki et al. |
| 7,225,032 B2 | 5/2007 | Schmeling et al. |
| 7,228,178 B2 | 6/2007 | Carroll |
| 7,239,921 B2 | 7/2007 | Canfield et al. |
| 7,242,982 B2 | 7/2007 | Singhal et al. |
| 7,254,449 B2 | 8/2007 | Karunasiri |
| 7,263,402 B2 | 8/2007 | Thacker et al. |
| 7,277,748 B2 | 10/2007 | Wingeier et al. |
| 7,277,749 B2 | 10/2007 | Gordon et al. |
| 7,286,880 B2 | 10/2007 | Olson et al. |
| 7,286,881 B2 | 10/2007 | Schommer et al. |
| 7,289,853 B1 | 10/2007 | Campbell et al. |
| 7,292,890 B2 | 11/2007 | Whitehurst et al. |
| 7,308,316 B2 | 12/2007 | Schommer |
| 7,324,852 B2 | 1/2008 | Barolat et al. |
| 7,324,853 B2 | 1/2008 | Ayal |
| 7,330,756 B2 | 2/2008 | Mamfeldt |
| 7,337,007 B2 | 2/2008 | Nathan et al. |
| 7,342,508 B2 | 3/2008 | Morgan et al. |
| 7,363,087 B2 | 4/2008 | Nghiem et al. |
| 7,376,466 B2 | 5/2008 | He et al. |
| 7,389,145 B2 | 6/2008 | Kilgore et al. |
| 7,483,748 B2 | 1/2009 | Torgerson et al. |
| 7,483,752 B2 | 1/2009 | Von arx et al. |
| 7,489,561 B2 | 2/2009 | Armstrong et al. |
| 7,502,652 B2 | 3/2009 | Gaunt et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,536,226 B2 | 5/2009 | Williams |
| 7,539,538 B2 | 5/2009 | Parramon et al. |
| 7,561,921 B2 | 7/2009 | Phillips et al. |
| 7,565,204 B2 | 7/2009 | Matei |
| 7,628,750 B2 | 12/2009 | Cohen |
| 7,630,771 B2 | 12/2009 | Cauller |
| 7,634,313 B1 | 12/2009 | Kroll et al. |
| 7,643,147 B2 | 1/2010 | Pless |
| 7,647,117 B2 | 1/2010 | Bauhahn |
| 7,650,192 B2 | 1/2010 | Wahlstrand |
| 7,655,014 B2 | 2/2010 | Ko et al. |
| 7,657,311 B2 | 2/2010 | Bardy et al. |
| 7,657,317 B2 | 2/2010 | Thacker et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,680,540 B2 | 3/2010 | Jensen et al. |
| 7,711,434 B2 | 5/2010 | Denker et al. |
| 7,736,379 B2 | 6/2010 | Ewers et al. |
| 7,747,325 B2 | 6/2010 | Dilorenzo |
| 7,780,625 B2 | 8/2010 | Bardy |
| 7,797,050 B2 | 9/2010 | Libbus et al. |
| 7,801,602 B2 | 9/2010 | McClure et al. |
| 7,803,142 B2 | 9/2010 | Longson et al. |
| 7,809,437 B2 | 10/2010 | Palmer et al. |
| 7,817,280 B2 | 10/2010 | Pless |
| 7,822,480 B2 | 10/2010 | Park et al. |
| 7,848,818 B2 | 12/2010 | Barolat et al. |
| 7,869,867 B2 | 1/2011 | Armstrong et al. |
| 7,894,905 B2 | 2/2011 | Pless et al. |
| 7,899,547 B1 | 3/2011 | Emadi et al. |
| 7,899,556 B2 | 3/2011 | Nathan et al. |
| 7,904,171 B2 | 3/2011 | Parramon et al. |
| 7,912,551 B2 | 3/2011 | Wosmek |
| 7,917,226 B2 | 5/2011 | Nghiem |
| 7,937,148 B2 | 5/2011 | Jacobson |
| 7,941,218 B2 | 5/2011 | Sambelashvili et al. |
| 7,962,211 B2 | 6/2011 | Torgerson et al. |
| 7,962,220 B2 | 6/2011 | Kolafa et al. |
| 7,974,706 B2 | 7/2011 | Moffitt et al. |
| 7,979,126 B2 | 7/2011 | Payne et al. |
| 7,991,467 B2 | 8/2011 | Markowitz et al. |
| 7,996,079 B2 | 8/2011 | Armstrong |
| 7,996,089 B2 | 8/2011 | Haugland et al. |
| 7,996,092 B2 | 8/2011 | Mrva et al. |
| 8,005,547 B2 | 8/2011 | Forsberg et al. |
| 8,019,443 B2 | 9/2011 | Scheicher et al. |
| 8,050,771 B2 | 11/2011 | Yamamoto et al. |
| 8,055,336 B1 | 11/2011 | Schulman et al. |
| 8,055,350 B2 | 11/2011 | Roberts |
| 7,925,350 B1 | 12/2011 | Palmer |
| 8,075,556 B2 | 12/2011 | Betts |
| 8,086,313 B2 | 12/2011 | Singhal et al. |
| 8,090,438 B2 | 1/2012 | Bardy et al. |
| 8,115,448 B2 | 2/2012 | John |
| 8,127,424 B2 | 3/2012 | Haller et al. |
| 8,131,377 B2 | 3/2012 | Shhi et al. |
| 8,140,168 B2 | 3/2012 | Olson et al. |
| 8,170,675 B2 | 5/2012 | Alataris et al. |
| 8,170,681 B2 | 5/2012 | Jimenez et al. |
| 8,175,719 B2 | 5/2012 | Shi et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,229,567 B2 | 7/2012 | Phillips et al. |
| 8,244,367 B2 | 8/2012 | Wahlstrand et al. |
| 8,255,057 B2 | 8/2012 | Fang et al. |
| 8,260,432 B2 | 9/2012 | DiGiore et al. |
| 8,265,770 B2 | 9/2012 | Toy et al. |
| 8,306,627 B2 | 11/2012 | Armstrong |
| 8,311,638 B2 | 11/2012 | Aghassian |
| 8,321,028 B1 | 11/2012 | Thenuwara et al. |
| 8,335,569 B2 | 12/2012 | Aghassian |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,267 B2 | 1/2013 | Schleicher et al. |
| 8,369,963 B2 | 2/2013 | Parramon et al. |
| 8,374,700 B2 | 2/2013 | Haubrich et al. |
| 8,386,047 B2 | 2/2013 | Koester |
| 8,386,048 B2 | 2/2013 | McClure et al. |
| 8,396,559 B2 | 3/2013 | Alataris et al. |
| 8,428,731 B2 | 4/2013 | Armstrong |
| 8,428,744 B2 | 4/2013 | Stancer et al. |
| 8,428,746 B2 | 4/2013 | DiGiore et al. |
| 8,428,748 B2 | 4/2013 | Alataris et al. |
| 8,437,846 B2 | 5/2013 | Swoyer et al. |
| 8,437,853 B2 | 5/2013 | Inman et al. |
| 8,457,744 B2 | 6/2013 | Janzig et al. |
| 8,457,759 B2 | 6/2013 | Parker et al. |
| 8,463,404 B2 | 6/2013 | Levi et al. |
| 8,473,066 B2 | 6/2013 | Aghassian et al. |
| 8,478,420 B2 | 7/2013 | Armstrong et al. |
| 8,483,838 B2 | 7/2013 | Nghiem et al. |
| 8,483,845 B2 | 7/2013 | Sage |
| 8,494,640 B2 | 7/2013 | Peterson et al. |
| 8,494,650 B2 | 7/2013 | Glukhovsky et al. |
| 8,497,804 B2 | 7/2013 | Haubrich et al. |
| 8,498,716 B2 | 7/2013 | Chen et al. |
| 8,509,905 B2 | 8/2013 | Alataris et al. |
| 8,509,906 B2 | 8/2013 | Walker et al. |
| 8,515,558 B1 | 8/2013 | Zweber et al. |
| 8,538,548 B2 | 9/2013 | Shi et al. |
| 8,543,200 B2 | 9/2013 | Lane et al. |
| 8,554,326 B2 | 10/2013 | Alataris et al. |
| 8,555,894 B2 | 10/2013 | Schulman et al. |
| 8,571,651 B2 | 10/2013 | Ben-ezra et al. |
| 8,577,474 B2 | 11/2013 | Rahman et al. |
| 8,588,933 B2 | 11/2013 | Floyd et al. |
| 8,612,014 B2 | 12/2013 | Rahman et al. |
| 8,612,019 B2 | 12/2013 | Moffitt |
| 8,620,435 B2 | 12/2013 | Rooney et al. |
| 8,620,449 B2 | 12/2013 | Zhao et al. |
| 8,626,310 B2 | 1/2014 | Barror et al. |

(56) References Cited

U.S. PATENT DOCUMENTS

| | | |
|---|---|---|
| 8,634,927 B2 | 1/2014 | Olson et al. |
| 8,644,947 B2 | 2/2014 | Zhu et al. |
| 8,644,948 B2 | 2/2014 | Grevious et al. |
| 8,649,874 B2 | 2/2014 | Alataris et al. |
| 8,660,655 B2 | 2/2014 | Peterson et al. |
| 8,666,491 B2 | 3/2014 | Chen et al. |
| 8,666,504 B2 | 3/2014 | Dronov et al. |
| 8,676,337 B2 | 3/2014 | Kallmyer |
| 8,676,341 B2 | 3/2014 | Kane et al. |
| 8,688,232 B2 | 4/2014 | Finley et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,780 B2 | 5/2014 | Lee |
| 8,718,781 B2 | 5/2014 | Alataris et al. |
| 8,718,782 B2 | 5/2014 | Alataris et al. |
| 8,738,145 B2 | 5/2014 | Goetz et al. |
| 8,750,985 B2 | 6/2014 | Parramon et al. |
| 8,751,009 B2 | 6/2014 | Wacnik |
| 8,755,893 B2 | 6/2014 | Gross et al. |
| 8,761,895 B2 | 6/2014 | Stevenson et al. |
| 8,768,472 B2 | 7/2014 | Fang et al. |
| 8,774,912 B2 | 7/2014 | Gerber |
| 8,774,926 B2 | 7/2014 | Alataris et al. |
| 8,788,045 B2 | 7/2014 | Gross et al. |
| 8,792,988 B2 | 7/2014 | Alataris et al. |
| 8,798,773 B2 | 8/2014 | Mashiach |
| 8,805,519 B2 | 8/2014 | Parker et al. |
| 8,812,135 B2 | 8/2014 | Mashiach |
| 8,843,203 B2 | 9/2014 | Lee et al. |
| 8,849,410 B2 | 9/2014 | Walker et al. |
| 8,849,412 B2 | 9/2014 | Perryman et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,219 B2 | 10/2014 | Trier et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,884,779 B2 | 11/2014 | Heiman et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,903,497 B2 | 12/2014 | Norgaard et al. |
| 8,903,499 B2 | 12/2014 | Pless et al. |
| 8,918,179 B2 | 12/2014 | Peterson et al. |
| 8,918,180 B2 | 12/2014 | Peterson |
| 8,923,988 B2 | 12/2014 | Bradley |
| 8,942,808 B2 | 1/2015 | Peterson et al. |
| 8,954,165 B2 | 2/2015 | Sharma et al. |
| 8,958,884 B2 | 2/2015 | Kothandaraman et al. |
| 8,958,891 B2 | 2/2015 | Kane et al. |
| 8,983,615 B2 | 3/2015 | Tahmasian et al. |
| 8,983,618 B2 | 3/2015 | Yamamoto et al. |
| 8,989,864 B2 | 3/2015 | Funderburk et al. |
| 8,989,868 B2 | 3/2015 | Mashiach et al. |
| 8,994,325 B2 | 3/2015 | Carbunaru et al. |
| 8,996,115 B2 | 3/2015 | Trier et al. |
| 9,002,445 B2 | 4/2015 | Chen |
| 9,002,460 B2 | 4/2015 | Parker |
| 9,002,461 B2 | 4/2015 | Walker et al. |
| 9,002,466 B2 | 4/2015 | Trier et al. |
| 9,020,599 B2 | 4/2015 | Rooney et al. |
| 9,020,602 B2 | 4/2015 | Aghassian |
| 9,026,227 B2 | 5/2015 | Daglow |
| 9,030,159 B2 | 5/2015 | Chen et al. |
| 9,031,666 B2 | 5/2015 | Fell |
| 9,037,261 B2 | 5/2015 | Bradley |
| 9,042,997 B2 | 5/2015 | Rahman et al. |
| 9,044,616 B2 | 6/2015 | Chen et al. |
| 9,056,206 B2 | 6/2015 | Torgerson et al. |
| 9,061,140 B2 | 6/2015 | Shi et al. |
| 9,061,151 B2 | 6/2015 | Mashiach et al. |
| 9,061,159 B2 | 6/2015 | Rahman |
| 9,061,162 B2 | 6/2015 | Mashiach et al. |
| 9,067,072 B2 | 6/2015 | Tahmasian et al. |
| 9,070,507 B2 | 6/2015 | Dronov et al. |
| 9,072,896 B2 | 7/2015 | Dar et al. |
| 9,079,041 B2 | 7/2015 | Park et al. |
| 9,084,900 B2 | 7/2015 | Hershey et al. |
| 9,089,712 B2 | 7/2015 | Joshi et al. |
| 9,095,726 B2 | 8/2015 | Parramon et al. |
| 9,101,774 B2 | 8/2015 | Mashiach et al. |
| 9,119,969 B2 | 9/2015 | Vansickle |
| 9,142,989 B2 | 9/2015 | Fell et al. |
| 9,149,635 B2 | 10/2015 | Denison et al. |
| 9,149,643 B2 | 10/2015 | Tahmasian et al. |
| 9,154,219 B2 | 10/2015 | Polefko et al. |
| 9,155,899 B2 | 10/2015 | Mashiach et al. |
| 9,155,901 B2 | 10/2015 | Dearden et al. |
| 9,162,068 B2 | 10/2015 | Dronov |
| 9,174,051 B2 | 11/2015 | Mamfeldt et al. |
| 9,174,053 B2 | 11/2015 | Zhu |
| 9,186,504 B2 | 11/2015 | Gross |
| 9,192,770 B2 | 11/2015 | Wang et al. |
| 9,199,083 B2 | 12/2015 | Caparso et al. |
| 9,211,418 B2 | 12/2015 | Aghassian |
| 9,216,297 B2 | 12/2015 | Kast et al. |
| 9,220,907 B2 | 12/2015 | Mashiach et al. |
| 9,220,909 B2 | 12/2015 | Carbunaru et al. |
| 9,220,910 B2 | 12/2015 | Colborn |
| 9,225,194 B2 | 12/2015 | Joshi |
| 9,227,075 B2 | 1/2016 | Aghassian et al. |
| 9,232,903 B2 | 1/2016 | Pless et al. |
| 9,238,138 B2 | 1/2016 | Lee et al. |
| 9,240,630 B2 | 1/2016 | Joshi |
| 9,242,106 B2 | 1/2016 | Kloster et al. |
| 9,248,279 B2 | 2/2016 | Chen et al. |
| 9,248,292 B2 | 2/2016 | Trier et al. |
| 9,248,302 B2 | 2/2016 | Mashiach et al. |
| 9,254,393 B2 | 2/2016 | Perryman et al. |
| 9,259,571 B2 | 2/2016 | Straka et al. |
| 9,259,582 B2 | 2/2016 | Joshi et al. |
| 9,259,584 B2 | 2/2016 | Bauhahn et al. |
| 9,265,941 B2 | 2/2016 | Van Den Biggelaar et al. |
| 9,265,958 B2 | 2/2016 | Joshi et al. |
| 9,289,616 B2 | 3/2016 | Koester |
| 9,295,841 B2 | 3/2016 | Fang et al. |
| 9,295,850 B2 | 3/2016 | Kallmyer |
| 9,314,613 B2 | 4/2016 | Mashiach |
| 9,314,628 B2 | 4/2016 | North et al. |
| 9,314,642 B2 | 4/2016 | Ozawa et al. |
| 9,320,847 B2 | 4/2016 | Rooney et al. |
| 9,320,899 B2 | 4/2016 | Parramon et al. |
| 9,320,908 B2 | 4/2016 | Fletcher et al. |
| 9,333,367 B2 | 5/2016 | Chen |
| 9,339,660 B2 | 5/2016 | Feldman et al. |
| 9,343,923 B2 | 5/2016 | Joshi |
| 9,352,161 B2 | 5/2016 | Thacker et al. |
| 9,370,664 B2 | 6/2016 | Mamfeldt et al. |
| 9,375,582 B2 | 6/2016 | Kaula et al. |
| 9,381,360 B2 | 7/2016 | Hershey |
| 9,387,331 B2 | 7/2016 | Zhao et al. |
| 9,387,332 B2 | 7/2016 | Zhao et al. |
| 9,393,423 B2 | 7/2016 | Parramon et al. |
| 9,393,428 B2 | 7/2016 | Nyberg, II et al. |
| 9,393,435 B2 | 7/2016 | Mashiach |
| 9,398,901 B2 | 7/2016 | Tischendorf et al. |
| 9,399,130 B2 | 7/2016 | Bonde et al. |
| 9,399,131 B2 | 7/2016 | Digiore et al. |
| 9,399,143 B2 | 7/2016 | Yamamoto et al. |
| 9,403,013 B2 | 8/2016 | Walker et al. |
| 9,403,020 B2 | 8/2016 | Wingeier |
| 9,403,021 B2 | 8/2016 | Dronov |
| 9,407,110 B2 | 8/2016 | Lui et al. |
| 9,409,029 B2 | 8/2016 | Perryman et al. |
| 9,435,830 B2 | 9/2016 | Joshi |
| 9,446,251 B1 | 9/2016 | Perryman et al. |
| 9,446,254 B2 | 9/2016 | Ozawa et al. |
| 9,449,501 B2 | 9/2016 | Grevious et al. |
| 9,452,288 B2 | 9/2016 | Whitehurst et al. |
| 9,457,186 B2 | 10/2016 | Gross |

(56) References Cited

U.S. PATENT DOCUMENTS

| | | | |
|---|---|---|---|
| 9,463,321 B2 | 10/2016 | Bradley et al. |
| 9,463,323 B2 | 10/2016 | Lee et al. |
| 9,463,326 B2 | 10/2016 | Ranu |
| 9,468,771 B2 | 10/2016 | Griffith et al. |
| 9,468,772 B2 | 10/2016 | Demmer |
| 9,469,437 B2 | 10/2016 | Kamath |
| 9,474,905 B2 | 10/2016 | Doan et al. |
| 9,480,841 B2 | 11/2016 | Hershey et al. |
| 9,504,832 B2 | 11/2016 | Libbus et al. |
| 9,504,838 B2 | 11/2016 | Rao et al. |
| 9,517,344 B1 | 12/2016 | Bradley |
| 9,517,352 B2 | 12/2016 | Kast et al. |
| 9,522,270 B2 | 12/2016 | Perryman et al. |
| 9,533,148 B2 | 1/2017 | Carcieri |
| 9,533,153 B2 | 1/2017 | Libbus et al. |
| 9,533,154 B2 | 1/2017 | Kothandaraman et al. |
| 9,533,162 B2 | 1/2017 | Ter-Petrosyan et al. |
| 9,555,257 B2 | 1/2017 | Mashiach et al. |
| 9,561,365 B2 | 2/2017 | Shi et al. |
| 9,585,642 B2 | 3/2017 | Dinsmoor et al. |
| 9,586,054 B2 | 3/2017 | Aghassian |
| 9,592,385 B2 | 3/2017 | Kaula et al. |
| 9,597,516 B2 | 3/2017 | Lee et al. |
| 9,597,517 B2 | 3/2017 | Moffitt |
| 9,597,521 B2 | 3/2017 | Plotkin et al. |
| 9,610,450 B2 | 4/2017 | Zhao |
| 9,616,230 B2 | 4/2017 | Grandhe |
| 9,623,244 B2 | 4/2017 | Kothandaraman |
| 9,623,245 B2 | 4/2017 | King et al. |
| 9,623,253 B2 | 4/2017 | Perryman et al. |
| 9,623,257 B2 | 4/2017 | Olson et al. |
| 9,630,231 B2 | 4/2017 | Kelsch et al. |
| 9,636,508 B2 | 5/2017 | Chen et al. |
| 9,643,022 B2 | 5/2017 | Mashiach et al. |
| 9,649,049 B2 | 5/2017 | Pless et al. |
| 9,649,493 B2 | 5/2017 | Mashiach |
| 9,653,941 B2 | 5/2017 | Dinsmoor et al. |
| 9,656,076 B2 | 5/2017 | Trier et al. |
| 9,656,081 B2 | 5/2017 | Feldman et al. |
| 9,675,809 B2 | 6/2017 | Chow |
| 9,687,649 B2 | 6/2017 | Thacker |
| 9,700,725 B2 | 7/2017 | Zhu |
| 9,700,730 B2 | 7/2017 | Carbunaru et al. |
| 9,707,404 B2 | 7/2017 | Rao et al. |
| 9,713,707 B2 | 7/2017 | Oron et al. |
| 9,713,717 B2 | 7/2017 | Aghassian |
| 9,713,718 B2 | 7/2017 | Lamont et al. |
| 9,713,721 B2 | 7/2017 | Kothandaraman |
| 9,724,513 B2 | 8/2017 | Lane et al. |
| 9,731,116 B2 | 8/2017 | Chen |
| 9,737,703 B2 | 8/2017 | Carbunaru et al. |
| 9,737,714 B2 | 8/2017 | Zottola |
| 9,744,347 B2 | 8/2017 | Chen et al. |
| 9,744,362 B2 | 8/2017 | Steinke et al. |
| 9,744,365 B2 | 8/2017 | Davis et al. |
| 9,744,368 B2 | 8/2017 | Dinsmoor |
| 9,750,930 B2 | 9/2017 | Chen |
| 9,782,588 B2 | 10/2017 | Shi et al. |
| 9,782,593 B2 | 10/2017 | Parramon et al. |
| 9,782,596 B2 | 10/2017 | Vamos et al. |
| 9,789,314 B2 | 10/2017 | Perryman et al. |
| 9,789,321 B2 | 10/2017 | Dixit et al. |
| 9,789,324 B2 | 10/2017 | Bauhahn et al. |
| 9,802,038 B2 | 10/2017 | Lee et al. |
| 9,802,048 B2 | 10/2017 | Armstrong |
| 9,802,052 B2 | 10/2017 | Mamfeldt |
| 9,814,458 B2 | 11/2017 | North |
| 9,814,880 B2 | 11/2017 | Hershey et al. |
| 9,814,884 B2 | 11/2017 | Parker et al. |
| 9,839,786 B2 | 12/2017 | Rondoni et al. |
| 9,844,677 B2 | 12/2017 | Aghassian |
| 9,849,298 B2 | 12/2017 | Ozawa et al. |
| 9,855,436 B2 | 1/2018 | Dearden et al. |
| 9,861,812 B2 | 1/2018 | Gross et al. |
| 9,861,825 B2 | 1/2018 | Ozawa et al. |
| 9,867,989 B2 | 1/2018 | Blum et al. |
| 9,867,994 B2 | 1/2018 | Parramon |
| 9,878,158 B2 | 1/2018 | Hershey et al. |
| 9,913,980 B2 | 3/2018 | Ostroff et al. |
| 9,913,986 B2 | 3/2018 | Chow et al. |
| 9,913,990 B2 | 3/2018 | Ter-petrosyan et al. |
| 9,925,381 B2 | 3/2018 | Nassif |
| 9,929,584 B2 | 3/2018 | Aghassian et al. |
| 9,931,107 B2 | 4/2018 | Tischendorf et al. |
| 9,935,498 B2 | 4/2018 | Joshi |
| 9,943,685 B2 | 4/2018 | Ramesh et al. |
| 9,950,166 B2 | 4/2018 | Mashiach et al. |
| 9,950,173 B2 | 4/2018 | Doan |
| 9,950,179 B2 | 4/2018 | Bonde et al. |
| 9,956,419 B2 | 5/2018 | Bokil |
| 9,956,421 B2 | 5/2018 | Bunyan et al. |
| 9,974,965 B2 | 5/2018 | Perryman et al. |
| 9,981,130 B2 | 5/2018 | Lee |
| 9,993,645 B2 | 6/2018 | Walker et al. |
| 10,004,896 B2 | 6/2018 | Oron et al. |
| 10,010,717 B2 | 7/2018 | Aghassian et al. |
| 10,014,571 B2 | 7/2018 | Andersen et al. |
| 10,056,688 B2 | 8/2018 | Andersen et al. |
| 10,058,705 B2 | 8/2018 | Andersen et al. |
| 10,064,288 B2 | 8/2018 | Li et al. |
| 10,080,902 B2 | 9/2018 | Dinsmoor et al. |
| 10,105,542 B2 | 10/2018 | Jiang et al. |
| 10,105,543 B2 | 10/2018 | Mamfeldt et al. |
| 10,118,040 B2 | 11/2018 | Zhu |
| 10,143,845 B2 | 12/2018 | Kothandaraman |
| 10,149,976 B1 | 12/2018 | Andresen et al. |
| 10,173,062 B2 | 1/2019 | Parker |
| 10,177,609 B2 | 1/2019 | Olson et al. |
| 10,179,241 B2 | 1/2019 | Walker et al. |
| 10,182,807 B2 | 1/2019 | Bridgeman et al. |
| 10,195,425 B2 | 2/2019 | Ostroff et al. |
| 10,213,608 B2 | 2/2019 | Moffitt |
| 10,219,229 B1 | 2/2019 | Mulligan, IV |
| 10,226,637 B2 | 3/2019 | Aghassian et al. |
| 10,238,863 B2 | 3/2019 | Gross et al. |
| 10,532,208 B2 | 1/2020 | Ostroff et al. |
| 10,583,284 B2 | 3/2020 | Peters et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2002/0183805 A1 | 12/2002 | Fang et al. |
| 2002/0183817 A1 | 12/2002 | Van Venrooij et al. |
| 2003/0014016 A1 | 1/2003 | Purdy |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0114905 A1 | 6/2003 | Kuzma |
| 2003/0176898 A1 | 9/2003 | Gross et al. |
| 2003/0236557 A1 | 12/2003 | Whitehurst et al. |
| 2003/0236558 A1 | 12/2003 | Whitehurst et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0254624 A1 | 6/2004 | Johnson |
| 2004/0167584 A1 | 8/2004 | Carroll et al. |
| 2004/0249431 A1 | 12/2004 | Ransbury et al. |
| 2004/0254612 A1 | 12/2004 | Ezra et al. |
| 2005/0113894 A1 | 5/2005 | Zilberman et al. |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2006/0085039 A1 | 4/2006 | Hastings et al. |
| 2006/0085042 A1 | 4/2006 | Hastings et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073354 A1 | 3/2007 | Knudson et al. |
| 2007/0083240 A1 | 4/2007 | Peterson et al. |
| 2007/0118196 A1* | 5/2007 | Rooney .......... A61N 1/0551 607/116 |

(56) References Cited

U.S. PATENT DOCUMENTS

| | | |
|---|---|---|
| 2007/0173893 A1 | 7/2007 | Pitts |
| 2007/0208392 A1 | 9/2007 | Kuschner et al. |
| 2007/0255369 A1 | 11/2007 | Bonde et al. |
| 2007/0293908 A1 | 12/2007 | Cowan et al. |
| 2007/0293912 A1 | 12/2007 | Cowan et al. |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0071178 A1 | 3/2008 | Greenland et al. |
| 2008/0091255 A1 | 4/2008 | Caparso et al. |
| 2008/0103407 A1 | 5/2008 | Bolea et al. |
| 2008/0103572 A1 | 5/2008 | Gerber |
| 2008/0109054 A1 | 5/2008 | Hastings et al. |
| 2008/0119911 A1 | 5/2008 | Rosero |
| 2008/0132964 A1 | 6/2008 | Cohen et al. |
| 2008/0269716 A1 | 10/2008 | Bonde et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0182402 A1 | 7/2009 | Glukhovsky |
| 2009/0204170 A1 | 8/2009 | Hastings et al. |
| 2009/0204173 A1 | 8/2009 | Fang et al. |
| 2009/0259280 A1 | 10/2009 | Wilkin et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0016911 A1 | 1/2010 | Willis et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0312320 A1 | 9/2010 | Faltys et al. |
| 2010/0280568 A1 | 11/2010 | Bulkes et al. |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0190849 A1* | 8/2011 | Faltys ............... A61N 1/36142 607/50 |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0224769 A1 | 9/2011 | Spenser et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0282412 A1 | 11/2011 | Glukhovsky et al. |
| 2011/0301670 A1 | 12/2011 | Gross |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2013/0192611 A1 | 8/2013 | Taepke, II et al. |
| 2013/0238066 A1* | 9/2013 | Boggs, II ............. A61N 1/0456 607/116 |
| 2013/0325081 A1 | 12/2013 | Karst et al. |
| 2013/0325084 A1 | 12/2013 | Lee |
| 2014/0214134 A1 | 7/2014 | Peterson |
| 2014/0296940 A1 | 10/2014 | Gross |
| 2015/0004709 A1 | 1/2015 | Nazarpoor |
| 2015/0018598 A1 | 1/2015 | Nabutovsky et al. |
| 2015/0018728 A1 | 1/2015 | Gross et al. |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0361544 A1 | 12/2016 | Oron et al. |
| 2017/0007829 A1 | 1/2017 | Gross |
| 2017/0119435 A1 | 5/2017 | Gross et al. |
| 2017/0128724 A1 | 5/2017 | Oron et al. |
| 2017/0136232 A1 | 5/2017 | Oron et al. |
| 2017/0224996 A1 | 8/2017 | Oron et al. |
| 2017/0232255 A1 | 8/2017 | Kent et al. |
| 2018/0126157 A1 | 5/2018 | Gross et al. |
| 2018/0140849 A1 | 5/2018 | Oron et al. |
| 2020/0046974 A1 | 2/2020 | Ostroff et al. |

FOREIGN PATENT DOCUMENTS

| | | |
|---|---|---|
| EP | 1533000 | 5/2005 |
| EP | 1703638 | 11/2012 |
| WO | 1998/010832 | 3/1998 |
| WO | 199/026530 | 6/1999 |
| WO | 01/10432 | 2/2001 |
| WO | 2001/010375 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 | 7/2013 |
| WO | 2013/111137 | 8/2013 |
| WO | 2013/156038 | 10/2013 |
| WO | 2013/164829 | 11/2013 |
| WO | 2014/068577 A2 | 5/2014 |
| WO | 2014/068577 A3 | 5/2014 |
| WO | 2014/087337 | 6/2014 |
| WO | 2014/167568 | 10/2014 |
| WO | 2015/004673 | 1/2015 |
| WO | 2014/081978 | 5/2015 |
| WO | 2016/028608 | 2/2016 |
| WO | 2016/157183 | 10/2016 |
| WO | 2016/172109 | 10/2016 |

OTHER PUBLICATIONS

An Office Action dated Feb. 7, 2019, which issued during the prosecution of U.S. Appl. No. 15/706,956.

An Office Action dated Jun. 26, 2019, which issued during the prosecution of U.S. Appl. No. 15/395,257.

An Office Action dated Dec. 5, 2018, which issued during the prosecution of U.S. Appl. No. 15/581,390.

Stuart, R. Morgan, and Christopher J. Winfree. "Neurostimulation techniques for painful peripheral nerve disorders." Neurosurgery Clinics of North America 20.1 (2009): 111-120.

Gofeld, Michael, and John G. Hanlon. "Ultrasound-Guided Placement of a Paddle Lead Onto Peripheral Nerves: Surgical Anatomy

(56) References Cited

OTHER PUBLICATIONS and Methodology." Neuromodulation: Technology at the Neural Interface 17.1 (2014): 48-53.
Alo, Kenneth M., et al. "Lumbar and sacral nerve root stimulation (NRS) in the treatment of chronic pain: a novel anatomic approach and neuro stimulation technique." Neuromudulation: Technology at the Neural Interface 2.1 (1999): 23-31.
C. de Balthasar, G. Cosendai, M. Hansen, D. Canfield, L. Chu, R. Davis, and J. Schulman, "Attachment of leads to RF-BION® microstimulators." Jul. 2005.
D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/2006/03/patents_galore.html (Downloaded Jan. 2012).
Chris Seper, "Neuros Medical Launches to Develop New Device to Block Amputee, Chronic Pain", Mar. 17, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchornisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/050069.
Naples GG et al., "A spiral nerve curff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).

(56) References Cited

OTHER PUBLICATIONS

Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, ED M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 lssue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
European Search Report dated Feb. 3, 2017, which issued during the prosecution of Applicant's European App No. 16196878.9.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract
A Notice of Allowance dated Jun. 9, 2014, which issued during the prosecution of U.S. Appl. No. 12/796,102.
A Notice of Allowance dated Apr. 25, 2014, which issued during the prosecution of U.S. Appl. No. 13/528,433.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
An Office Action dated Dec. 12, 2016, which issued during the prosecution of U.S. Appl. No. 14/939,418.
Brindley (1983) A technique for anodally blocking large nerve fibers.
An Office Action dated Sep. 26, 2013, which issued during the prosecution of U.S. Appl. No. 13/528,433.
DJOGlobal.com—Interferential Current Therapy (IFC).
A Notice of Allowance dated Jun. 15, 2017, which issued during the prosecution of U.S. Appl. No. 14/939,418.
A Notice of Allowance dated Mar. 22, 2017, which issued during the prosecution of U.S. Appl. No. 14/939,418.
A Notice of Allowance dated Feb. 15, 2018, which issued during the prosecution of U.S. Appl. No. 14/601,604.
A Notice of Allowance dated Jul. 16, 2018, which issued during the prosecution of U.S. Appl. No. 15/360,501.
A Notice of Allowance dated Sep. 1, 2017, which issued during the prosecution of U.S. Appl. No. 14/649,873.
U.S. Appl. No. 60/985,353, filed Nov. 5, 2007.
An Office Action dated May 19, 2017, which issued during the prosecution of U.S. Appl. No. 14/935,941.
electrotherapy.org—Interferential Therapy.
An Office Action dated Mar. 5, 2018, which issued during the prosecution of U.S. Appl. No. 15/360,501.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7
An Office Action dated Oct. 30, 2015, which issued during the prosecution of U.S. Appl. No. 14/226,723.
An Office Action dated Dec. 6, 2017, which issued during the prosecution of U.S. Appl. No. 14/601,604.
Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472
UCLA Team Reports Initial Success with Trigeminal Nerve Stimulation epilepsy. https://web.archive.org/web/20121020145122/https://www.epilepsy.com/epilepsy/newsletter/apr09_STIM.
Kucklick, Theodore R., ed. *The medical device R&D handbook*. Chapter 3—Intro to needles and cannulae. CRC Press, 2012.
Szmurlo, R., Starzynski, J., Wincenciak, S. and Rysz, A. (2009) 'Numerical model of vagus nerve electrical stimulation', *COMPEL—The international journal for computation and mathematics in electrical and electronic engineering*, 28(1), pp. 211-220.
An Office Action dated Apr. 5, 2017, which issued during the prosecution of U.S. Appl. No. 14/374,375.
An Office Action dated Apr. 4, 2017, which issued during the prosecution of U.S. Appl. No. 14/601,604.
An Office Action dated Feb. 27, 2017, which issued during the prosecution of U.S. Appl. No. 14/649,873.
An Office Action dated Aug. 8, 2016, which issued during the prosecution of U.S. Appl. No. 14/735,741.
An Office Action dated Nov. 21, 2016, which issued during the prosecution of U.S. Appl. No. 14/601,626.
Reggiani et al. "Biophysical effects of high frequency electrical field on muscle fibers in culture." (2009) pp. 49-56.
An Office Action dated Feb. 13, 2017, which issued during the prosecution of U.S. Appl. No. 14/601,604.
European Search Report dated Mar. 10, 2017, which issued during the prosecution of Applicant's European App No. 16196864.9.
U.S. Appl. No. 61/733,995, filed Dec. 6, 2012.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Injecta 2013 GmbH catalogue.
An Office Action dated Sep. 22, 2016, which issued during the prosecution of U.S. Appl. No. 14/374,375.

(56) References Cited

OTHER PUBLICATIONS

An Office Action dated Dec. 26, 2017, which issued the prosecution of U.S. Appl. No. 14/935,941.
An Office Action dated Jan. 8, 2018, which issued during the prosecution of U.S. Appl. No. 14/935,941.
An Office Action dated Nov. 30, 2017, which issued during the prosecution of U.S. Appl. No. 15/726,971.
An Office Action dated Jun. 4, 2018, which issued during the prosecution of U.S. Appl. No. 15/860,385.
Notice of Allowance dated Oct. 22, 2018, which issued during the prosecution of U.S. Appl. No. 15/860,385.
An Office Action dated Dec. 2, 2020, which issued during the prosecution of U.S. Appl. No. 16/166,383.

* cited by examiner

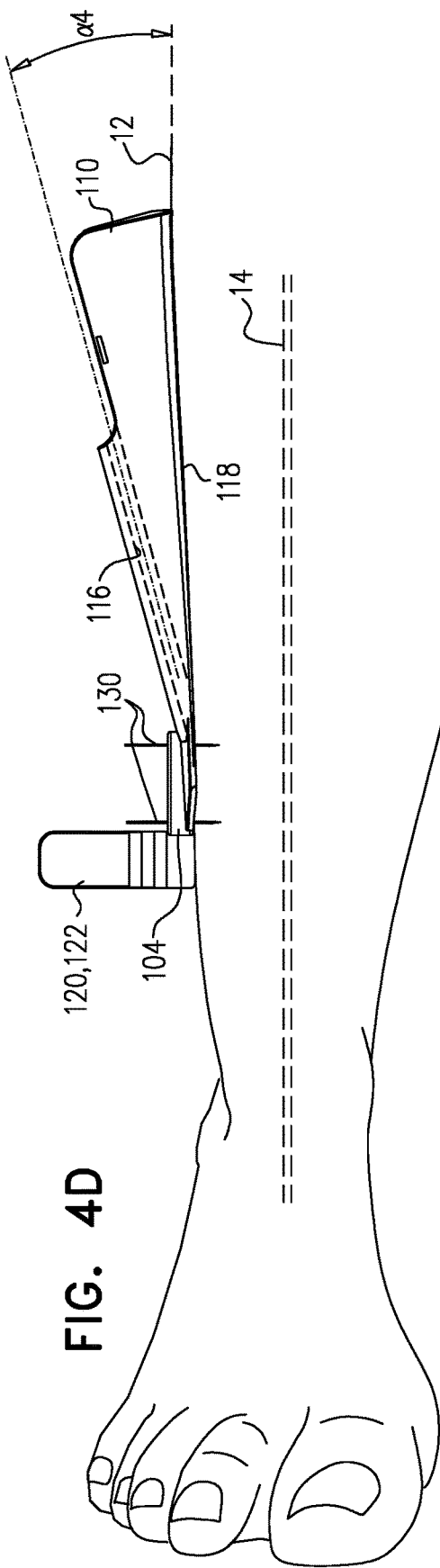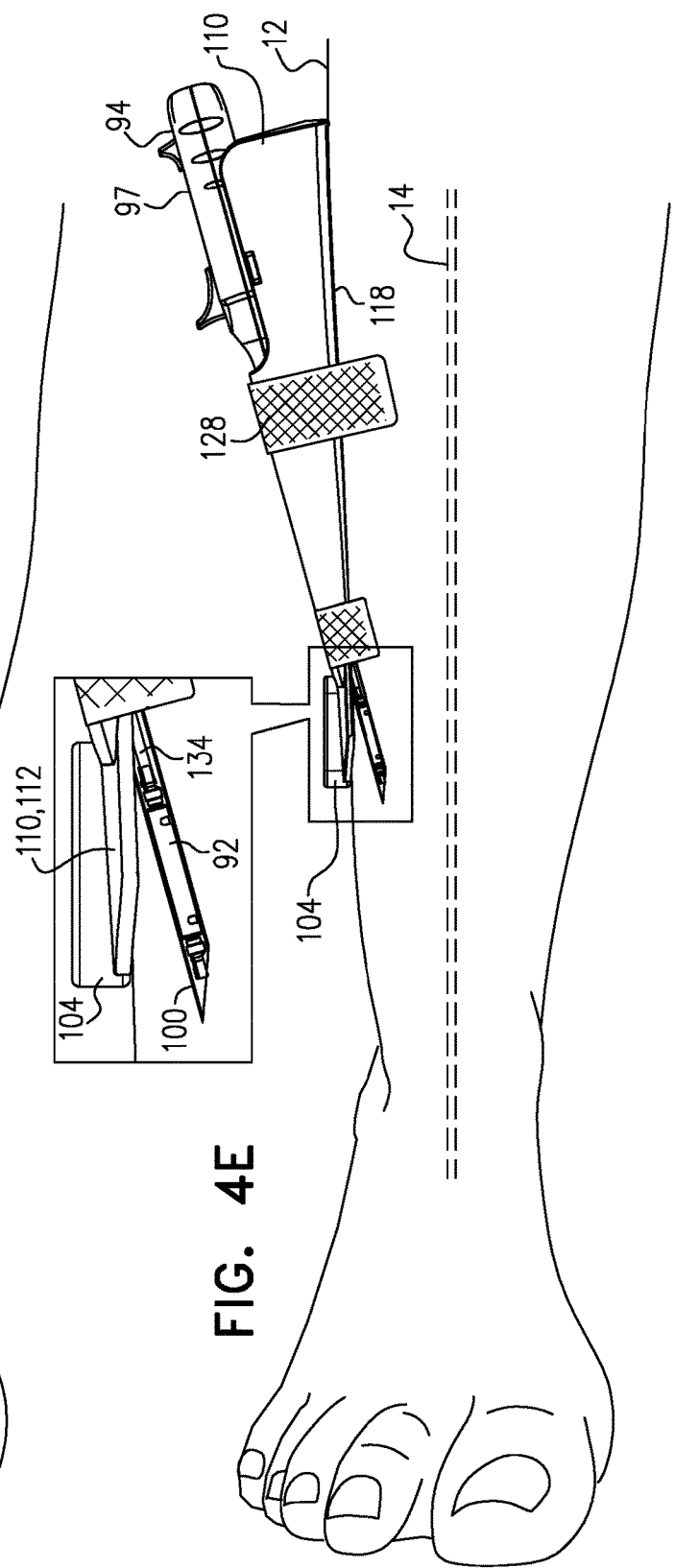

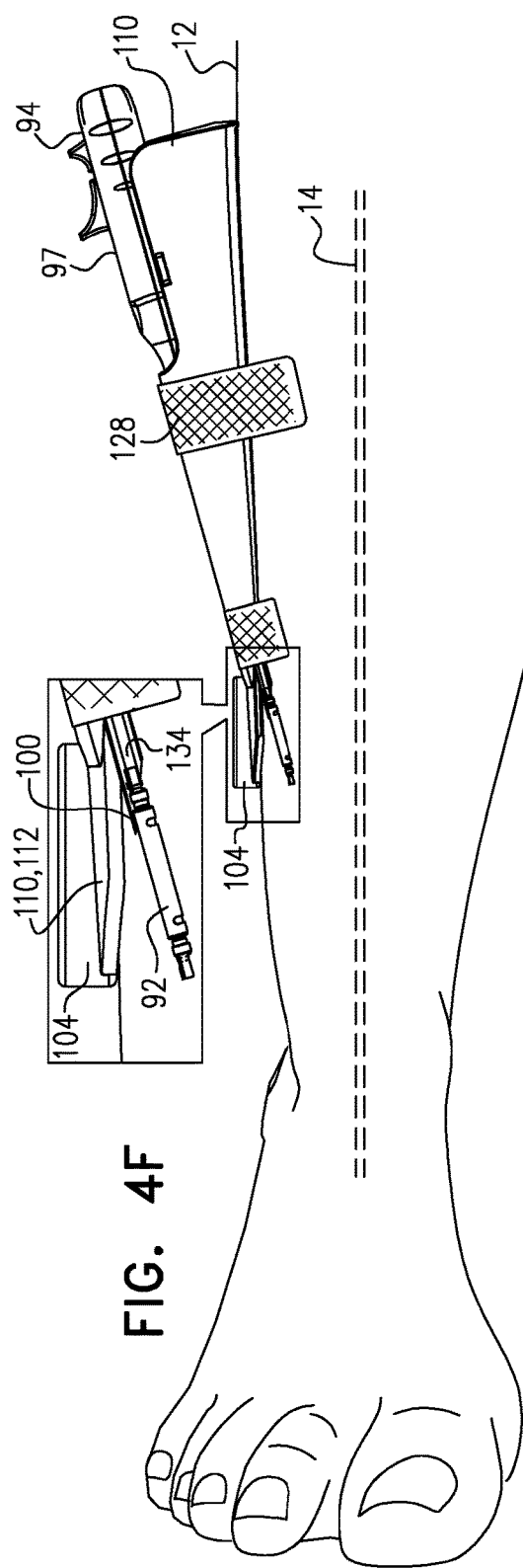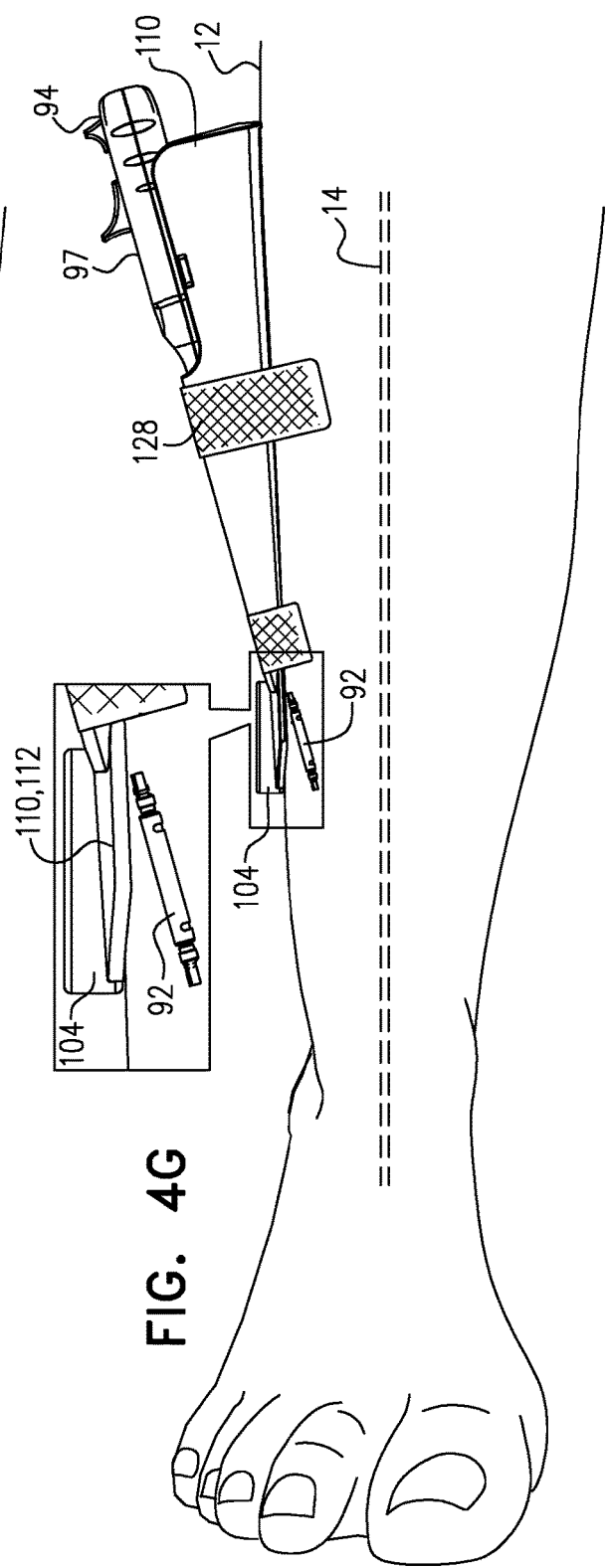

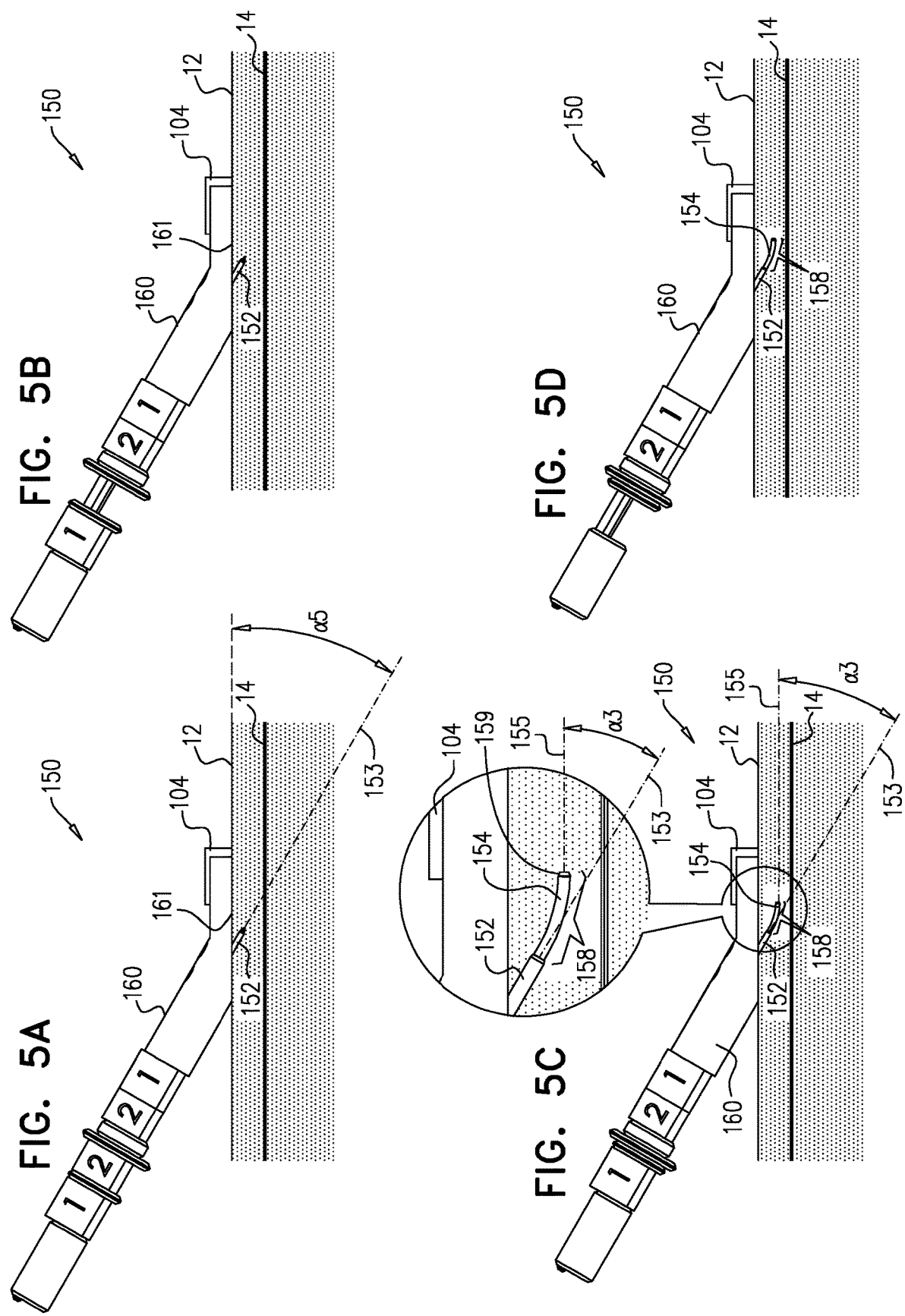

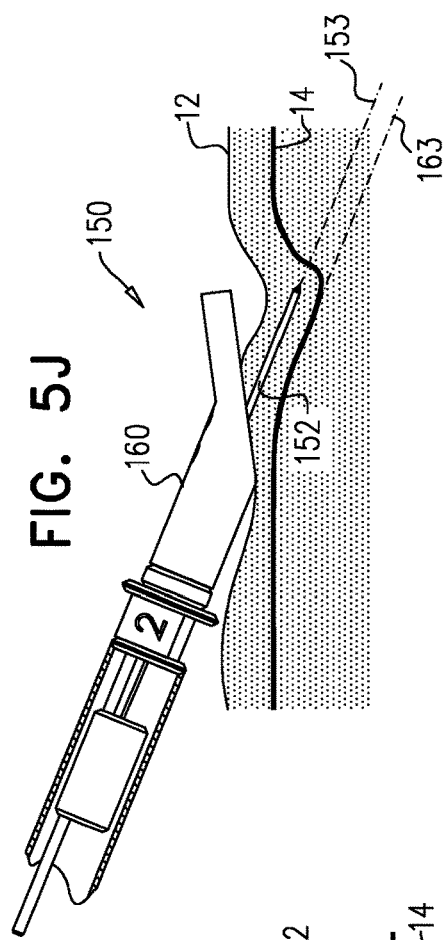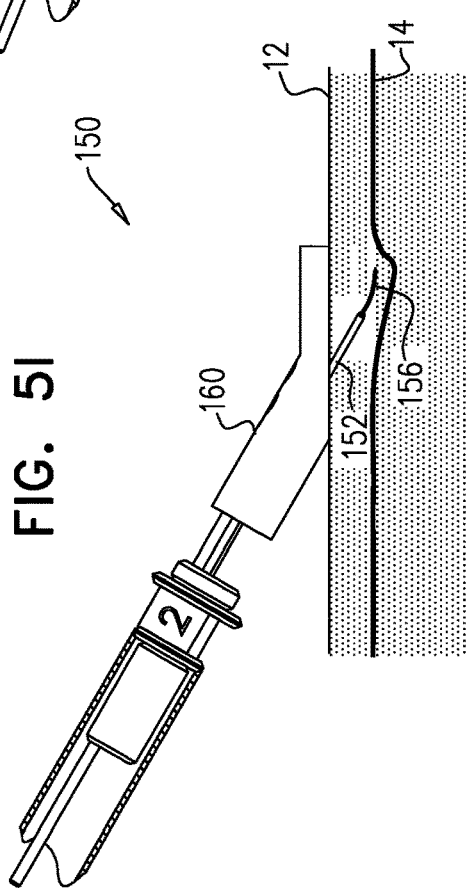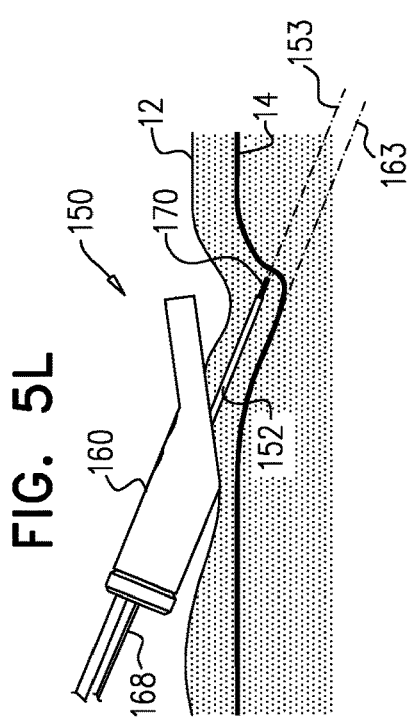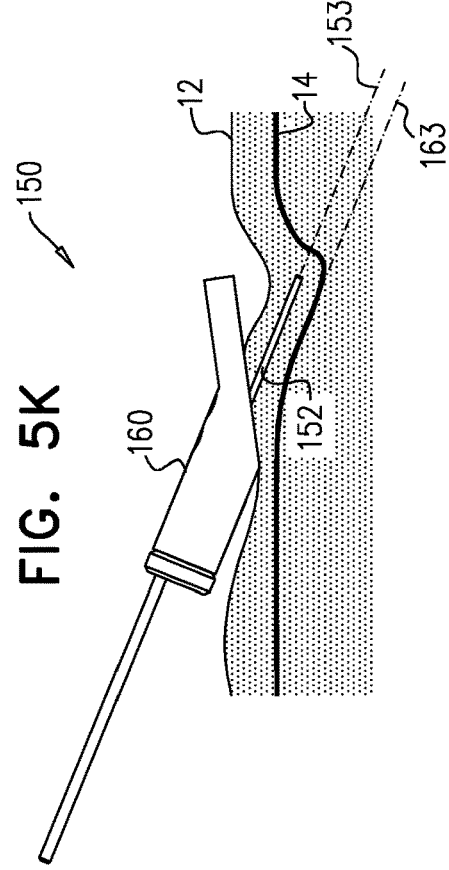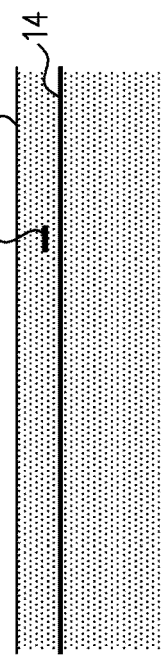

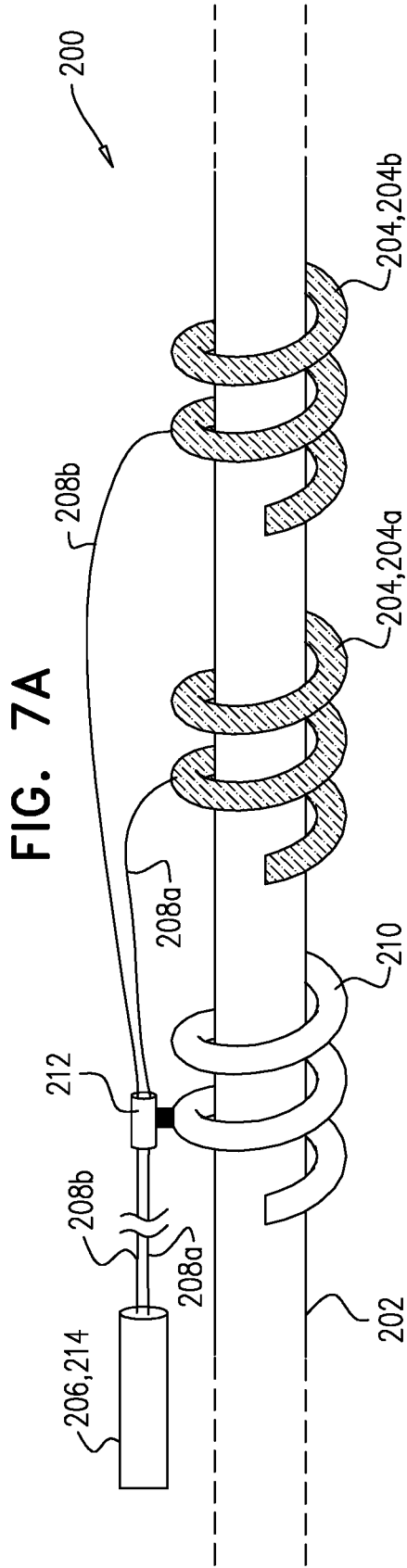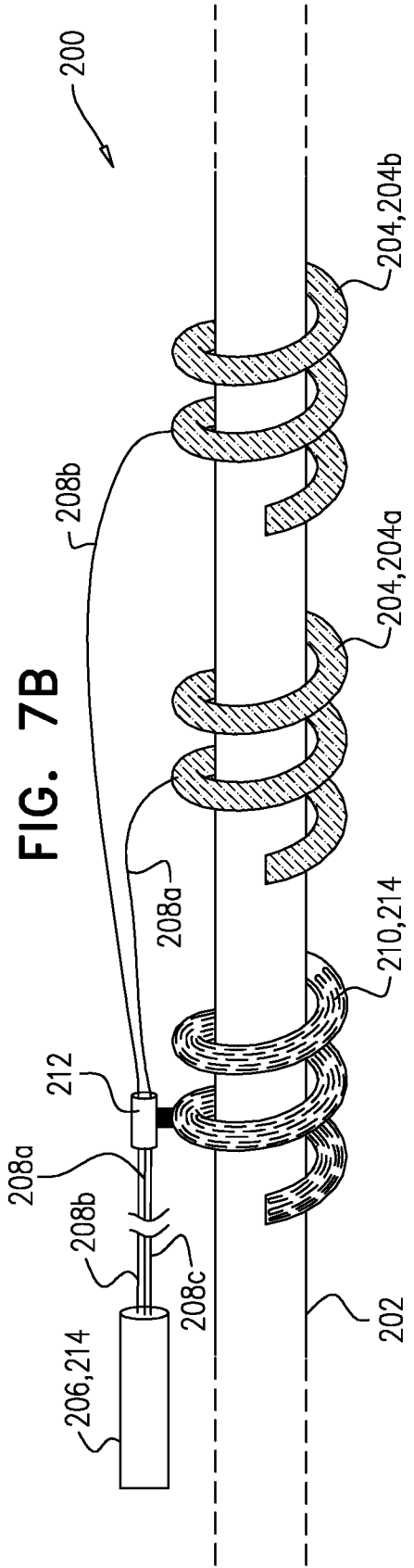

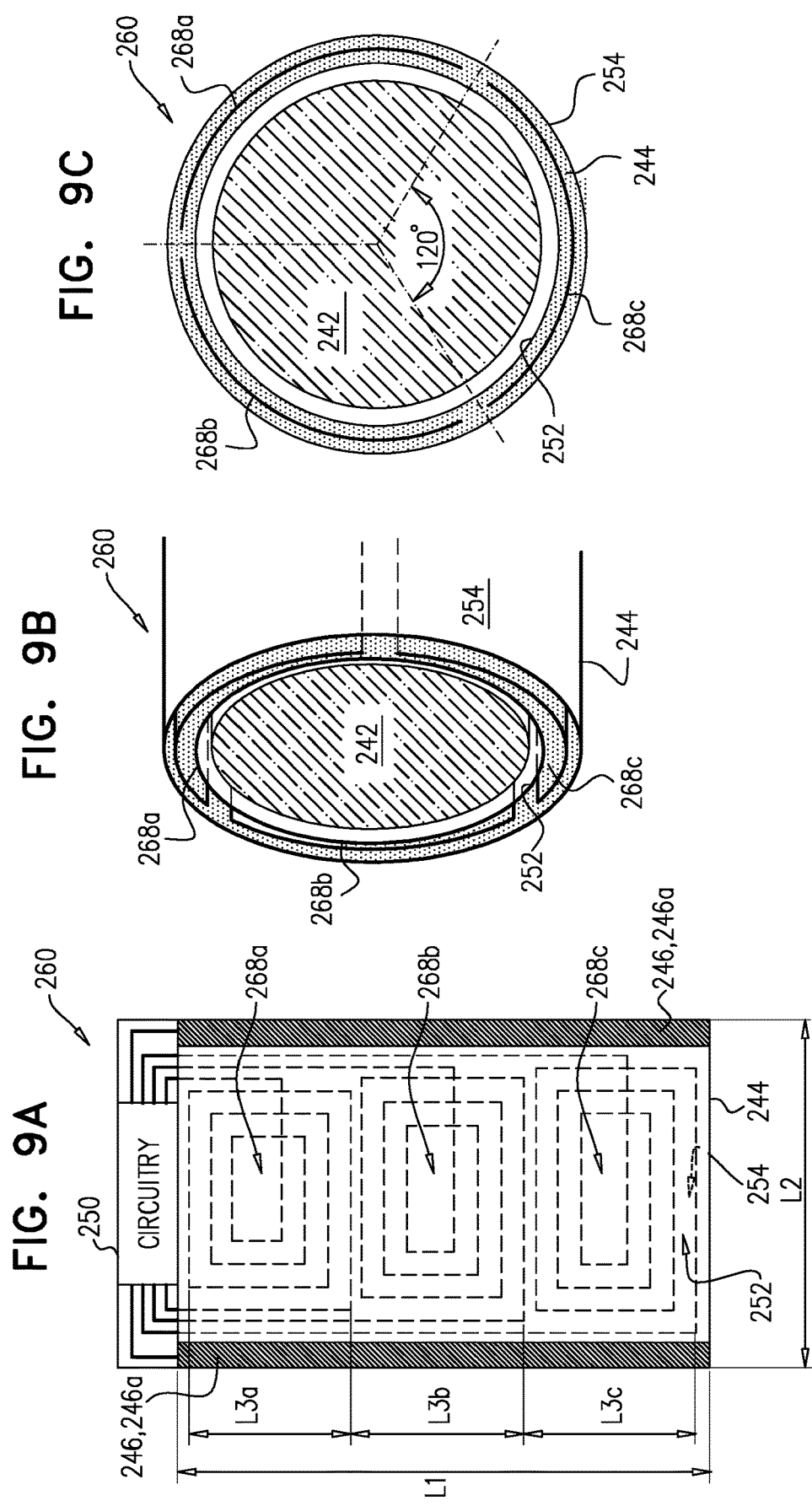

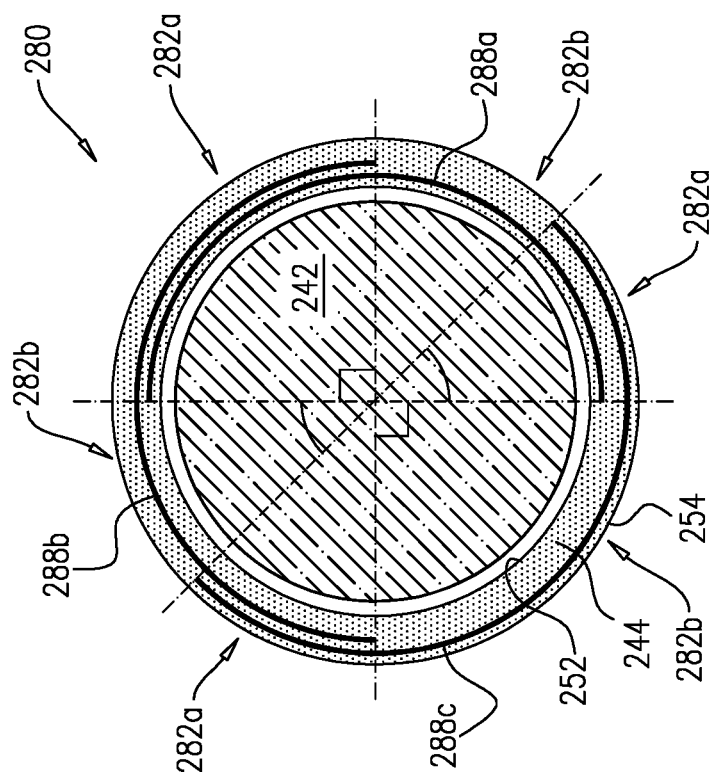
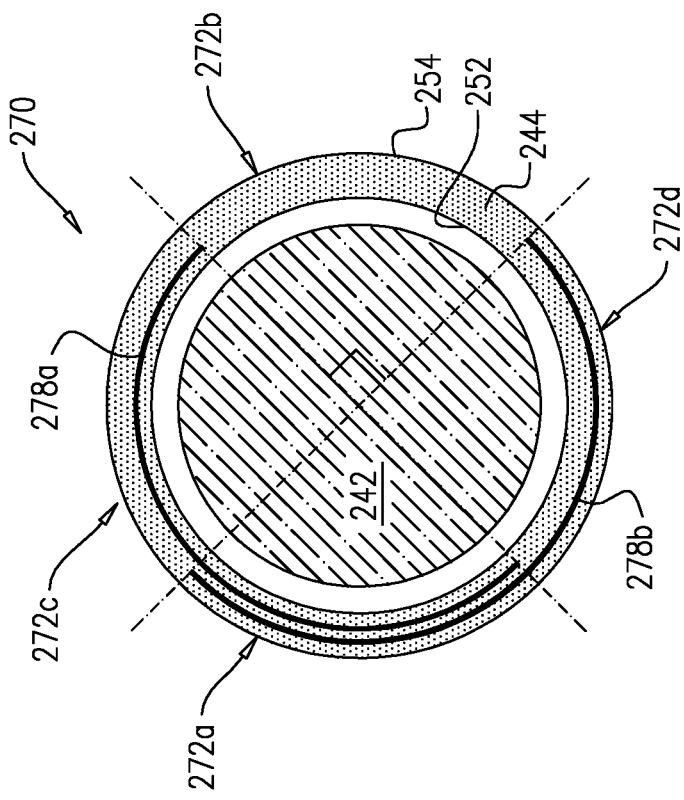

DELIVERY OF IMPLANTABLE NEUROSTIMULATORS

CROSS-REFERENCES TO RELATED APPLICATIONS

The present application is a Continuation of U.S. patent application Ser. No. 16/363,256 to Oron et al., filed Mar. 25, 2019, and entitled "Delivery of implantable neurostimulators," which published as US 2019/0217085 and which is a Continuation of U.S. patent application Ser. No. 15/860,385 to Gross et al., filed Jan. 2, 2018, and entitled "Delivery of implantable neurostimulators," (now U.S. Pat. No. 10,238,863) which is a Continuation of U.S. patent application Ser. No. 14/649,873 to Gross et al. (now U.S. Pat. No. 9,861,812), which is the US National Phase of PCT Application IB/2013/060607 to Gross et al., filed Dec. 3, 2013, which published as WO 2014/087337, and which claims priority from U.S. Provisional Patent Application 61/733,995 to Gross et al., filed on Dec. 6, 2012, and entitled "Delivery of implantable neurostimulators", which is incorporated herein by reference.

FIELD OF THE INVENTION

The present invention relates generally to medical devices, and specifically to apparatus and methods for use with percutaneous implants.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Other disorders may cause pain to adjacent tissues.

Neurostimulation is a clinical tool used to treat various neurological disorders. This technique involves modulation of the nervous system by electrically activating fibers in the body.

SUMMARY OF THE INVENTION

For some applications of the invention, apparatus and techniques are described for percutaneous delivery of an implant. For some applications, the apparatus and techniques facilitate identifying a target site and/or delivering the implant to the identified target site. For some applications, the apparatus and techniques facilitate implanting the implant at a given orientation with respect to the tissue in which the implant is implanted. For some applications, the apparatus and techniques facilitate anchoring the implant to the tissue in which the implant is implanted.

For some applications of the invention, a system comprising an injectable implant, at least one helical electrode, and at least one helical anchor is described. For some applications, the helical anchor comprises an antenna configured to wirelessly receive power.

For some applications of the invention, systems are described that comprise a nerve cuff having one or more planar antennas, configured to wirelessly receive power, and integral with a cuff body that is configured to be wrapped around a nerve of a subject. For some applications, the planar antennas span less than 360 degrees around the nerve. For some applications, a plurality of planar antennas together spans at least 360 degrees around the nerve, each of the plurality of planar antennas spanning less than 360 degrees (e.g., no more than 180 degrees) around the nerve. For some applications, the cuff body comprises a helical body, and the configuration of the planar antennas is projected onto the helical body.

There is therefore provided, in accordance with an application of the present invention, apparatus for facilitating percutaneous delivery of an implant to a tissue of a body of a subject, the implant being configured to apply a current to at least the tissue, the apparatus including:

an implant-storage member, configured to be percutaneously advanced to the tissue, and shaped to define:
   a space that is configured to house the implant,
   an opening through which the implant is deliverable to the tissue, and
   at least one window, configured such that, while the implant is disposed within the space and the implant-storage member is disposed in the tissue, the window facilitates flow of the current therethrough from the implant to the tissue; and a delivery manipulator, reversibly couplable to the implant, and configured to facilitate delivery of the implant through the opening.

In an application, the delivery manipulator is configured to facilitate delivery of the implant by remaining stationary with respect to the tissue while the implant-storage member is withdrawn proximally with respect to the tissue.

In an application, the implant-storage member includes a hollow needle.

In an application, the implant-storage member:
   has a proximal end,
   has a distal end that defines the opening, and
   has a lateral wall that defines the window between the proximal end and the distal end.

In an application, the delivery manipulator is slidably coupled to the proximal end of the implant-storage member, and is configured to push the implant through the opening.

In an application, the apparatus further includes the implant.

In an application, the apparatus further includes a longitudinal member:
   having a distal end configured to be percutaneously advanced into the subject while coupled to the implant,
   having a proximal end configured to be secured to a skin surface of the subject (1) while the distal end of the longitudinal member is coupled to the implant within the subject, and (2) for a duration of at least 1 day, and
   being configured to move the implant within the subject by being moved.

In an application:
   the implant includes at least two electrodes,
   the implant-storage member is shaped to define at least two windows, and
   the implant is configured to be disposed within the space such that each of the electrodes is aligned with a respective window.

There is further provided, in accordance with an application of the present invention, apparatus for facilitating percutaneous delivery of an implant to a target site in a body of a subject, facilitated by at least one transcutaneous electrode, the apparatus including:

a delivery tool, having a proximal portion and a distal portion, the distal portion including an implant-storage member, the implant-storage member configured to be percutaneously advanced toward the target site, and shaped to define (a) a space that is configured to house the implant, and (b) an opening through which the implant is advanceable;

a guide shaped to define at least one channel and configured to facilitate percutaneous advancement of the transcutaneous electrode, via the channel, to the target site; and a mount, configured:
to be placed on the skin of the subject in a predetermined position with respect to the channel, and
to be coupled to the delivery tool, the coupling of the mount to the delivery tool facilitating the delivery of the implant-storage member to the target site.

In an application, the delivery tool is configured to deliver the implant to the target site by, when the implant is disposed in the space, and the implant-storage member is disposed at the target site, withdrawing the implant-storage member proximally with respect to the target site while simultaneously holding the implant stationary with respect to the target site.

In an application, the apparatus further includes the transcutaneous electrode and an extracorporeal control unit, the extracorporeal control unit being configured to drive the transcutaneous electrode to apply a current to the tissue of the subject, so as to identify the target site.

In an application, the mount includes the guide.

In an application, the guide is configured to be placed on the skin of the subject, and the mount is configured to be placed in the given position with respect to the channel by being placed in a given position with respect to the guide.

In an application:
the guide has a first skin-contacting surface, and is shaped such that the channel is generally orthogonal to a plane defined by the skin-contacting surface, and
the mount has a second skin-contacting surface, and is shaped to define a lumen through which the implant-storage member is slidable, the lumen being disposed at less than 30 degrees with respect to the second skin-contacting surface.

In an application, the mount is configured to be coupled to the guide in the predetermined position with respect to the guide.

In an application, the mount is shaped to define a receptacle within which at least a portion of the guide is placeable.

In an application, the apparatus further includes a depth indicator, configured to indicate a depth of the transcutaneous electrode in the body of the subject.

In an application, the apparatus further includes the transcutaneous electrode.

In an application, the depth indicator includes a gauge, configured to be placed on the skin of the subject in a vicinity of the transcutaneous electrode.

In an application, the transcutaneous electrode includes markings, the depth indicator including the markings.

There is further provided, in accordance with an application of the present invention, apparatus for facilitating percutaneous delivery of an implant, the apparatus including:

a rigid delivery tube, having a distal end, a proximal end, and a longitudinal axis therebetween, and shaped to define a lumen configured to facilitate passage of the implant therethrough; and at least one flexible longitudinal member having a proximal portion and a distal portion:
slidably coupled to the rigid delivery tube,
configured to pierce tissue of the subject, and
having shape memory such that a distal tip of the flexible longitudinal member has a tendency to be disposed at a first nonzero angle with respect to the proximal portion, the apparatus having:
at least one retracted configuration in which the distal tip of the flexible longitudinal member is generally parallel with the longitudinal axis of the rigid delivery tube, and
an extended configuration in which the distal portion of the flexible longitudinal member is disposed distally to the distal end of the rigid delivery tube, and the distal tip of the flexible longitudinal member is disposed at a second nonzero angle with respect to the longitudinal axis of the rigid delivery tube.

In an application, the at least one flexible longitudinal member includes a flexible wire.

In an application, the at least one flexible longitudinal member is slidable through the lumen of the rigid delivery tube.

In an application, the at least one flexible longitudinal member includes nitinol.

In an application, the apparatus further includes a mount, having a skin-contacting surface configured to be placed on skin of the subject, the rigid delivery tube and the flexible longitudinal member being slidably coupled the mount.

In an application, the rigid delivery tube has an angular disposition with respect to a plane defined by the skin-contacting surface of between 30 and 45 degrees.

In an application, the apparatus is configured such that, in the extended configuration, an angular disposition of the distal tip of the flexible longitudinal member with respect to the plane is shallower than the angular disposition of the rigid delivery tube with respect to the plane.

In an application, the apparatus has a withdrawn retracted configuration, and an advanced retracted configuration in which the distal portion of the flexible longitudinal member and the distal end of the rigid delivery tube are disposed further from the mount than in the withdrawn retracted configuration.

In an application, the apparatus is configured such that, when (1) the mount is disposed on the skin of the subject, (2) the apparatus is in the extended configuration thereof, and (3) the flexible longitudinal member is disposed in the tissue of the subject, as the apparatus moves toward the advanced retracted configuration thereof, the apparatus distorts the tissue of the subject.

In an application, the at least one flexible longitudinal member includes a flexible tube.

In an application, the at least one flexible longitudinal member includes at least a first flexible longitudinal member that includes the flexible tube, and a second flexible longitudinal member, configured to pierce the tissue of the subject, and slidable through the flexible tube.

In an application, the second flexible longitudinal member includes a flexible wire.

There is further provided, in accordance with an application of the present invention, apparatus for implantation in tissue of a subject, the apparatus including:

an implant body, having a proximal end and a distal end, and a longitudinal axis between the proximal end and the distal end;

at least one electrode;

at least one distal anchor, configured to inhibit movement of the implant body through the tissue in a distal direction more than in a proximal direction; and at least one proximal anchor, disposed proximal to the distal anchor, and configured to inhibit movement of the implant body through the tissue in the proximal direction more than in the distal direction.

In an application:

the distal anchor includes at least one barb that protrudes, in the distal direction, at a nonzero angle with respect to the longitudinal axis of the implant body, and the proximal anchor includes at least one barb that protrudes, in the proximal direction, at a nonzero angle with respect to the longitudinal axis of the implant body.

In an application:

each of the anchors has a constrained state and an unconstrained state, each of the anchors is configured such that the nonzero angle of the barb of each anchor is smaller in the constrained state of the anchor than in the unconstrained state of the anchor.

In an application, the apparatus further includes:

an implant-storage member:

configured to be percutaneously advanced to the tissue, shaped to define a space that is configured to house the implant, and an opening through which the implant is bidirectionally movable, configured to constrain each of the anchors in the respective constrained state thereof while the respective anchor is disposed within the space, and configured to move the distal anchor into the constrained state thereof when the distal anchor is moved through the opening into the space; and a delivery manipulator, reversibly couplable to the implant, and configured to facilitate bidirectional movement of the implant through the opening.

There is further provided, in accordance with an application of the present invention, apparatus for use with a nerve of a subject, the apparatus including:

at least one helical electrode, configured to be wrapped around a first site on the nerve of the subject;

an injectable implant, configured to be percutaneously implanted in a vicinity of the nerve of the subject, and including a control unit that is configured to drive the at least one helical electrode to apply a current to the nerve of the subject;

at least one wire, coupling the injectable implant to the at least one helical electrode; and a helical anchor, configured to be wrapped around a second site of the nerve of the subject, and including a brace, the brace being coupled to a portion of the wire that is between the helical electrode and the injectable implant.

In an application:

the at least one helical electrode includes at least two helical electrodes, the at least one wire includes at least two wires, each wire coupling a respective one of the helical electrodes to the injectable implant, and the brace is configured to be coupled to a respective portion of each of the wires that is between the respective helical electrode and the injectable implant.

In an application, the helical anchor includes at least one antenna, configured to wirelessly receive energy, and the injectable implant is configured to receive the received energy from the antenna.

In an application, the control unit is configured to drive the at least one electrode in response to the received energy.

There is further provided, in accordance with an application of the present invention, apparatus for use with a nerve of a subject, the apparatus including:

a cuff body having:

first and second mutually-orthogonal lengths on a plane of the cuff body when the cuff body is unrolled, which define an area of the cuff body on the plane, and a first face, a second face, and a thickness between the first face and the second face, and being configured to be wrapped around the nerve such that the first face faces the nerve, and such that a length of the nerve covered by the cuff body is defined by the second length of the cuff body;

including at least one electrode, disposed on the first face of the cuff body; and including at least one planar antenna, coupled to the cuff body so as to be parallel with the plane of the cuff body, and configured to wirelessly receive energy; and circuitry, configured to use the received energy from the planar antenna to drive the at least one electrode to apply a current to the nerve.

In an application, the cuff body includes a material, and the planar antenna is disposed within the material of the cuff body.

In an application, the at least one planar antenna includes a plurality of planar antennas, and a sum of areas spanned by the plurality of planar antennas is greater than the area of the cuff body.

In an application, the at least one planar antenna includes n planar antennas, each of the n planar antennas spanning an area that has a length along the first length of the cuff body, that is greater than 1/n times the first length of the cuff body.

In an application, the at least one electrode includes two electrodes, the electrodes being disposed at opposite ends of the second length of the cuff body from each other.

In an application, each of the electrodes has a longest dimension that is parallel to the first length of the cuff body.

In an application, the cuff body is configured such that, when the cuff body is wrapped around the nerve, the cuff body defines a tube, the first face defining a 360-degree circumferential wall of the tube.

In an application, the at least one antenna spans an area, and the cuff body is configured such that, when the cuff body is wrapped around the nerve, a total number of degrees around the circumferential wall that the area of the at least one planar antenna spans, is at least 180 degrees.

In an application, the at least one antenna spans an area, and the cuff body is configured such that, when the cuff body is wrapped around the nerve, a total number of degrees around the circumferential wall that the area of the at least one planar antenna spans, is at least 360 degrees.

In an application, the cuff body is configured such that, when the cuff body is wrapped around the nerve, the area of the at least one planar antenna circumscribes the circumferential wall.

In an application, the at least one planar antenna includes a plurality of planar antennas, and the cuff body is configured such that, when the cuff body is wrapped around the nerve, the area of each of the planar antennas spans around less than 360 degrees of the circumferential wall.

In an application, the cuff body is configured such that, when the cuff body is wrapped around the nerve, the area of each of the planar antennas spans around less than 270 degrees of the circumferential wall.

In an application, the cuff body is configured such that, when the cuff body is wrapped around the nerve, the area of each of the planar antennas spans around between 90 and 180 degrees of the circumferential wall.

In an application, the cuff body is configured such that, when the cuff body is wrapped around the nerve, the area of each of the planar antennas spans around 180 degrees of the circumferential wall.

In an application, the cuff body is configured such that, when the cuff body is wrapped around the nerve, the area of each of the planar antennas is disposed around 120 degrees of the circumferential wall.

In an application, the plurality of planar antennas includes at least a first antenna and a second antenna, and the first antenna is rotationally offset around the circumferential wall with respect to the second antenna, by between 45 degrees and 180 degrees.

In an application, the plurality of planar antennas includes at least a first antenna and a second antenna, and the first antenna is rotationally offset around the circumferential wall with respect to the second antenna, by between 45 degrees and 60 degrees.

In an application, the plurality of planar antennas includes at least a first antenna and a second antenna, and the first antenna is rotationally offset around the circumferential wall with respect to the second antenna, by between 45 degrees and 90 degrees.

In an application, the plurality of planar antennas includes at least a first antenna and a second antenna, and the first antenna is rotationally offset around the circumferential wall with respect to the second antenna, by between 60 degrees and 120 degrees.

In an application, the plurality of planar antennas includes at least a first antenna and a second antenna, and the first antenna is rotationally offset around the circumferential wall with respect to the second antenna, by between 90 degrees and 120 degrees.

In an application, the at least one planar antenna includes n planar antennas, each of the n planar antennas spanning an area that has a length along the first length of the cuff body, that is generally 1/n times as great as the first length of the cuff body.

In an application, the n planar antennas include two planar antennas, each of the two planar antennas spanning an area that has a length along the first length of the cuff body that is half as great as the first length of the cuff body.

In an application, the area of each of the n planar antennas overlaps the area of at least another of the n planar antennas.

In an application, the at least one planar antenna includes a plurality of planar antennas that includes at least a first planar antenna and a second planar antenna, the first planar antenna spanning a first area, and the second planar antenna spanning a second area.

In an application, the first area and the second area do not overlap.

In an application, the first area and the second area overlap.

In an application, the first area has length along the first length of the cuff body, the second area has length along the first length of the cuff body, and the length of the first area overlaps the length of the second area.

There is further provided, in accordance with an application of the present invention, apparatus for use with a nerve of a subject, the nerve having a longitudinal axis, the apparatus including:

a cuff body, configured to be wrapped at least 360 degrees around the longitudinal axis; and a plurality of planar antennas, configured to wirelessly receive power, the plurality of planar antennas being coupled to the cuff body such that, when the cuff body is wrapped around the 360 degrees, each of the planar antennas spans less than 360 degrees around the longitudinal axis.

In an application, at least one of the planar antennas is disposed in each rotational position around the longitudinal axis.

In an application, when the cuff body is wrapped around the 360 degrees, at least two of the planar antennas are disposed at a same longitudinal site.

In an application, when the cuff body is wrapped around the 360 degrees of portion of the nerve, at least a first one of the planar antennas is disposed at a first longitudinal site of the longitudinal axis, and at least a second one of the planar antennas is disposed at a second longitudinal site of the longitudinal axis that is different to the first longitudinal site.

In an application, when the cuff body is wrapped around the 360 degrees, each of the planar antennas spans no more than 270 degrees around the longitudinal axis.

In an application, when the cuff body is wrapped around the 360 degrees, each of the planar antennas spans between 90 and 180 degrees around the longitudinal axis.

There is further provided, in accordance with an application of the present invention, apparatus for implantation in a vicinity of a tissue of a subject, the apparatus including:

an implant body, configured to be percutaneously delivered to the vicinity of the tissue;

at least one suction chamber, shaped to define at least one window; and at least one anchor disposed within the suction chamber, the anchor:

defining a tissue-piercing element, having a first state and a second state, and being transitionable from the first state to the second state, and being configured such that when the anchor transitions from the first state toward the second state, the tissue-piercing element moves with respect to the window.

In an application, the first state includes a constrained state, the apparatus including a constraining member, configured to constrain the anchor in the constrained state, and the anchor is configured to automatically transition toward the unconstrained state when the constraining member stops constraining the anchor.

In an application, the apparatus is configured to draw a portion of the tissue through the window into the suction chamber when an at least partial vacuum is drawn into the suction chamber, and the tissue-piercing element is configured to penetrate the portion of the tissue when the anchor transitions from the first state toward the second state.

There is further provided, in accordance with an application of the present invention, a method for use with a subject, the method including:

inserting, through skin of the subject and into tissue of the subject, an implant-storage member and an implant, the implant-storage member being shaped to define a space configured to house the implant, a distal opening, and at least one window;

while the implant is disposed within the space, driving a current, using the implant, into tissue of the subject through the at least one window;

removing the implant from the space via the distal opening by proximally withdrawing the implant-storage member.

In an application, proximally withdrawing the implant-storage member includes leaving a longitudinal member coupled to the implant such that a distal portion of the longitudinal member is disposed in the tissue, and the method further includes securing a proximal portion of the longitudinal member to a skin surface of the subject.

In an application, inserting includes inserting such that the implant is disposed at a first site of the tissue, driving the current includes driving a first application of the current and the method further includes:

after a start of the driving of the first application of the current, measuring a parameter of the subject; and subsequently to the measuring and prior to the removing, moving the implant to a second site of the tissue, and subsequently driving a second application of the current.

In an application, driving the current includes wirelessly powering the implant to drive the current.

In an application, removing the implant includes removing the implant by proximally withdrawing the implant-storage member while providing a reference force to the implant using a delivery manipulator, reversibly coupled to the implant.

In an application, the implant-storage member has a lateral wall that defines the at least one window, and driving the current includes driving the current through the at least one window in the lateral wall.

In an application, the implant includes at least two electrodes, the lateral wall defines at least two windows, and driving the current includes driving the current via the at least two electrodes while each electrode is aligned with a respective window.

There is further provided, in accordance with an application of the present invention, a method, including:

placing, on skin of a subject, a guide shaped to define at least one channel;

advancing at least one transcutaneous electrode through the at least one channel and percutaneously toward a target site in tissue of the subject;

driving the at least one electrode to apply an electrical current to the tissue of the subject, and detecting a parameter of the subject that varies in response to the applying of the electrical current;

at least in part responsively to the detected parameter, measuring a depth of the transcutaneous electrode in the tissue using a depth indicator;

at least in part responsively to the measured depth, placing a mount on the skin of the subject and in a predetermined position with respect to the channel; and while the mount is in the predetermined position with respect to the channel, delivering to the target site, using a delivery tool coupled to the mount, an implant disposed within a space defined by an implant-storage member at a distal end of the delivery tool, the delivery being facilitated by the coupling of the delivery tool to the mount.

In an application, the method further includes, subsequently to delivering, moving the implant out of the space via an opening defined by the implant-storage member by withdrawing the implant-storage member proximally while holding the implant stationary with respect to the target site.

In an application, placing the mount includes placing the mount subsequently to driving the at least one electrode to apply the electrical current.

In an application, the method further includes, subsequently to placing the mount, coupling the delivery tool to the mount and advancing the implant-storage member through a lumen defined by the mount.

In an application, the mount includes the guide, and placing the mount includes placing the mount at the same time as placing the guide.

In an application:

advancing the at least one electrode percutaneously includes advancing the at least one electrode percutaneously at an angle that is generally orthogonal to a plane defined by a first skin-contacting surface of the guide, and delivering the implant includes advancing the implant-storage member percutaneously at an angle that is less than 30 degrees with respect to a second skin-contacting surface defined by the mount.

In an application, placing the mount in the predetermined position includes coupling the mount to the guide in the predetermined position.

In an application, placing the mount in the predetermined position includes placing a receptacle defined by the mount around at least a portion of the guide.

In an application, the depth indicator includes a gauge, and measuring the depth includes placing the gauge on the skin of the subject in a vicinity of the transcutaneous element.

In an application, the method further includes, subsequently to measuring the depth, and prior to placing the mount, selecting the mount from a plurality of mounts at least in part responsively to the measured depth.

In an application, the method further includes, subsequently to measuring the depth, adjusting the mount at least in part responsively to the measured depth.

There is further provided, in accordance with an application of the present invention, a method, including:

percutaneously advancing at least one flexible longitudinal member through tissue of a subject such that shape memory of the flexible longitudinal member disposes a distal tip of the flexible longitudinal member at a nonzero angle with respect to a proximal portion of the flexible longitudinal member;

subsequently, distally advancing a rigid delivery tube along the flexible longitudinal member and into the tissue, such that the apparatus moves into a retracted configuration in which the distal tip of the flexible longitudinal member is generally parallel with a longitudinal axis of the rigid delivery tube; and subsequently, delivering an implant to the tissue via the rigid delivery tube.

In an application, percutaneously advancing the at least one flexible longitudinal member includes piercing the tissue with the at least one flexible longitudinal member.

In an application, advancing the at least one flexible longitudinal member includes advancing a flexible wire.

In an application, advancing the at least one flexible longitudinal member includes advancing the at least one flexible longitudinal member through the rigid delivery tube, and advancing the rigid delivery tube includes sliding the rigid delivery tube over the at least one flexible longitudinal member.

In an application, advancing the at least one flexible longitudinal member includes advancing at least one flexible longitudinal member that includes nitinol.

In an application, the method further includes placing a skin-contacting surface of a mount on skin of the subject, and advancing the at least one flexible longitudinal member includes sliding the at least one flexible longitudinal member with respect to the mount, and advancing the rigid delivery tube includes sliding the rigid delivery tube with respect to the mount.

In an application, sliding the rigid delivery tube with respect to the mount includes sliding the rigid delivery tube at an angular disposition, with respect to a plane defined by the skin-contacting surface, of between 30 and 45 degrees.

In an application, advancing the rigid delivery tube along the flexible longitudinal member includes increasing an angular disposition of the distal tip of the flexible longitudinal member with respect to the plane.

In an application, advancing the rigid delivery tube along the flexible longitudinal member includes deforming the tissue of the subject.

In an application, delivering the implant includes delivering the implant while the tissue is deformed, and the method further includes, subsequently to delivering the implant, withdrawing the rigid delivery tube from the tissue.

In an application, advancing the at least one flexible longitudinal member includes advancing a flexible tube.

In an application, advancing the flexible tube includes advancing a first flexible longitudinal member, and further includes advancing a second flexible longitudinal member through the flexible tube and into the tissue.

In an application, advancing the second flexible longitudinal member includes advancing a flexible wire.

There is further provided, in accordance with an application of the present invention, a method, including:

percutaneously delivering an implant into a subject;

drawing tissue of the subject via a window of the implant into a suction chamber of the implant; and driving an anchor having a tissue-piercing element through the tissue within the suction chamber, the tissue-piercing element remaining within suction chamber.

There is further provided, in accordance with an application of the present invention, apparatus for use with a subject, including:

an implant, configured to be percutaneously injected into tissue of the subject; and a longitudinal member, reversibly couplable to the implant, and:

the apparatus is configured to be left, for at least 1 day, in a state in which:

the implant is disposed within the tissue, a distal portion of the longitudinal member is coupled to the implant, a proximal portion of the longitudinal member is secured to a skin surface of the subject, and the implant is movable within the subject by moving the proximal portion of the longitudinal member.

The present invention will be more fully understood from the following detailed description of applications thereof, taken together with the drawings, in which:

BRIEF DESCRIPTION OF THE DRAWINGS

FIGS. 4A-H are schematic illustrations of a system for facilitating percutaneous delivery of an implant to a target site in the body of a subject, in accordance with some applications of the invention;

FIGS. 5A-M are schematic illustrations of a system for facilitating percutaneous delivery of an implant, the system comprising a rigid delivery tube and at least a first flexible longitudinal member, slidably coupled to the delivery tube, in accordance with some applications of the invention;

FIGS. 7A-B are schematic illustrations of a system for use with a nerve of a subject, in accordance with some applications of the invention;

FIGS. 9A-C are schematic illustrations of a system for use with nerve, in accordance with some applications of the invention;

FIGS. 10-14 are schematic illustrations of planar antenna configurations, in accordance with respective applications of the invention;

DETAILED DESCRIPTION OF EMBODIMENTS

Figure 1A:
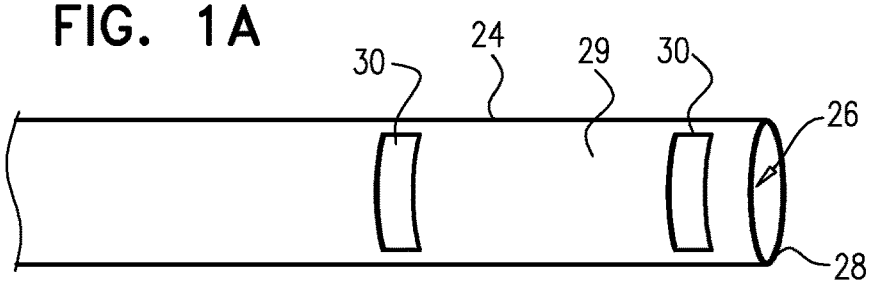
FIGS. 1A-D are schematic illustrations of a system for facilitating delivery of an implant in a tissue of a subject, in accordance with some applications of the invention.
Figure 1B:
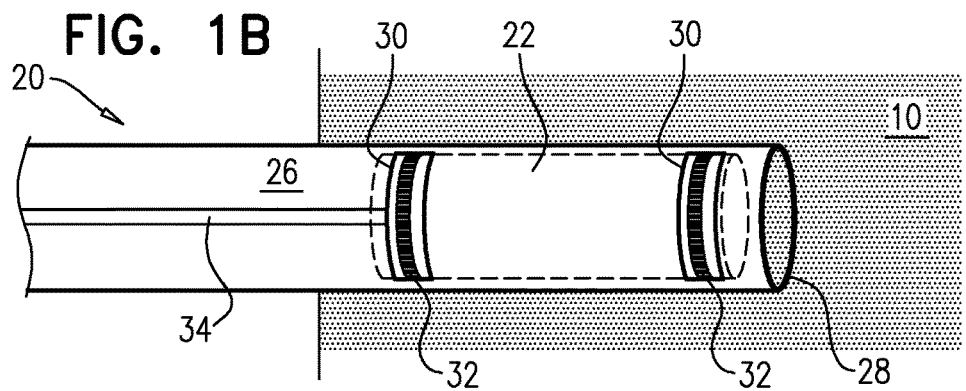
Figure 1C:
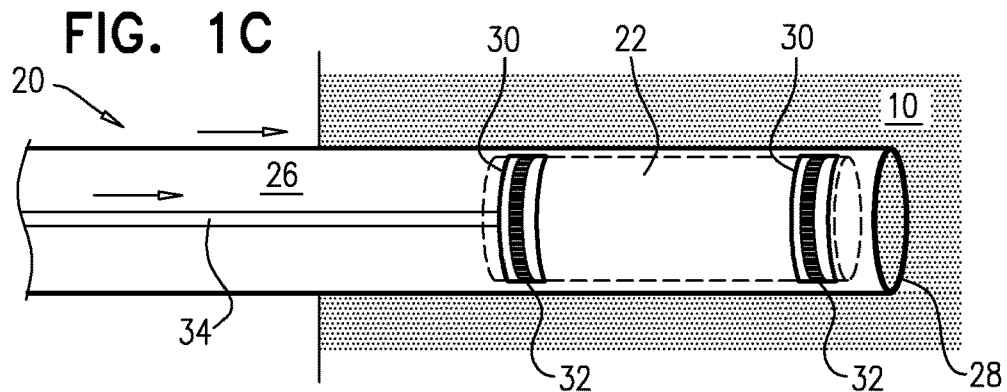
Figure 1D:
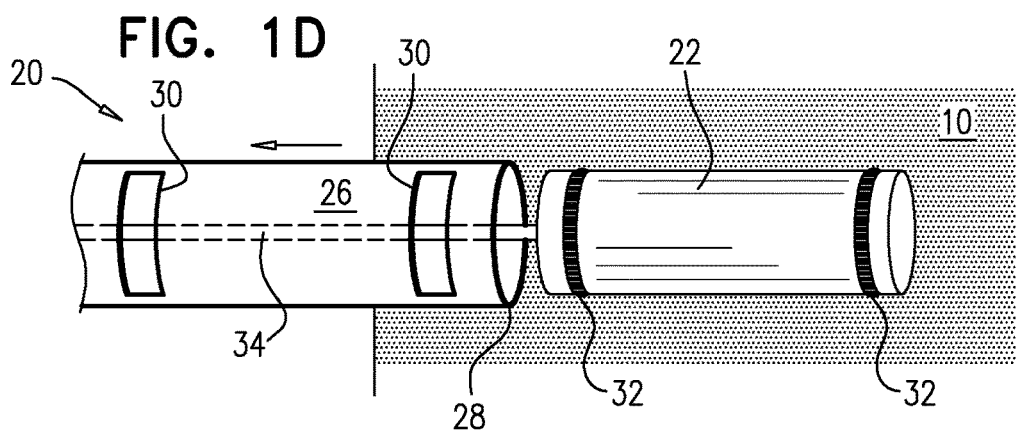

Reference is made to FIGS. 1A-D, which are schematic illustrations of a system 20 for facilitating delivery of an implant 22 in a tissue 10 of a subject, in accordance with some applications of the invention. System 20 comprises an implant-storage member 24, which typically comprises a tubular member. FIG. 1A shows member 24 alone, and FIGS. 1B-D show member 24 being used in combination with other components of system 20, to delivery implant 20 to tissue 10.

Implant-storage member 24 is shaped to define a space 26, configured to house implant 22. For some applications in which member 24 comprises a tubular member, space 26 comprises at least part of a lumen that extends the length of the tubular member, from a proximal end to a distal end thereof. For some applications, member 24 comprises a hollow needle. Implant-storage member 24 is shaped to further define an opening 28, configured to facilitate passage of implant 22 therethrough, and at least one window 30. Typically, member 24 comprises a lateral wall 29, that extends from the proximal end to the distal end of member 24, and that is shaped to define window 30.

Typically, implant 22 comprises at least one electrode 32, and is configured to apply a current (e.g., a treatment current) to the subject (e.g., to tissue 10, or to a different target tissue, or anatomical site or structure, such as to a nerve of the subject). Further typically, implant 22 comprises two or more electrodes 32, and implant-storage member 24 is shaped to define two or more respective windows 30, positioned such that, when implant 22 is housed within space 26, each electrode is aligned with a respective window. Member 24 (e.g., windows 30 thereof) is configured to facilitate application of the current by implant 22 (e.g., to the tissue), while implant 22 is disposed in space 26. Member 24 thereby facilitates the positioning of implant 22 at a preferred location within tissue 10 (e.g., in a vicinity of a target tissue, such as in a location in which the current has maximal effect on a physiological parameter of the subject), prior to deployment of the implant through opening 28. That is, a response to the current driven by implant 22 may be detected, and according to that response, the implant is deployed.

FIG. 1B shows implant-storage member 24, housing implant 22, having been percutaneously delivered to a first site within tissue 10. Electrodes 32 of implant 22 are aligned with windows 30. Electrodes 32 drive the current (e.g., into tissue 10), and the physiological parameter is measured (e.g., after a start of the application of the current, such as during the application of the current or after the application of the current). If the response to the current is acceptable (e.g., greater than a threshold response), the implant may be deployed. Alternatively, as shown in FIG. 1C, member 24 may be repositioned within tissue 10 (e.g., to a second site within the tissue, such as a deeper site), until an acceptable response is achieved, at which point implant 22 is deployed. As shown in FIG. 1D, implant 22 is typically deployed by holding implant 22 still with respect to tissue 10 (e.g., using a delivery manipulator 34 that is reversibly couplable to the implant), while withdrawing implant-storage member 24 proximally, such that the implant is delivered through opening 28.

Typically, implant 22 is wirelessly powered, and is configured to apply the current in response to receiving the wireless power. For some applications, the driving of the current described with reference to FIGS. 1B and 1C is driven in this wireless manner. For some application, the driving of the current described with reference to FIGS. 1B and 1C is driven by a control unit via a wire disposed within manipulator 34. For example, it may be desirable to identify a suitable position for implant 22 within tissue 10 independently of any variables caused by the use of wireless power, and only subsequently test and/or calibrate the transmission and/or reception of the wireless power.

Reference is made to FIGS. 2A-G, which are schematic illustrations of a system 50, comprising an implant 52, which comprises an implant body 53, at least one electrode 56 (e.g., two electrodes 56) and one or more directionally-biased anchors 54, in accordance with some applications of the invention. Implant 52 comprises one or more proximal anchors 54a at a distal portion of the implant, and typically further comprises one or more distal anchors 54b at a proximal portion of the implant, typically disposed in the opposite orientation to anchors 54a. Distal anchors 54a are configured to inhibit movement of the implant (e.g., of implant body 53) through tissue 10, in a distal direction more than in a proximal direction. Similarly, proximal anchors 54b are configured to inhibit movement of the implant in a through the tissue, in the proximal direction more than in the distal direction.

Figure 2A:
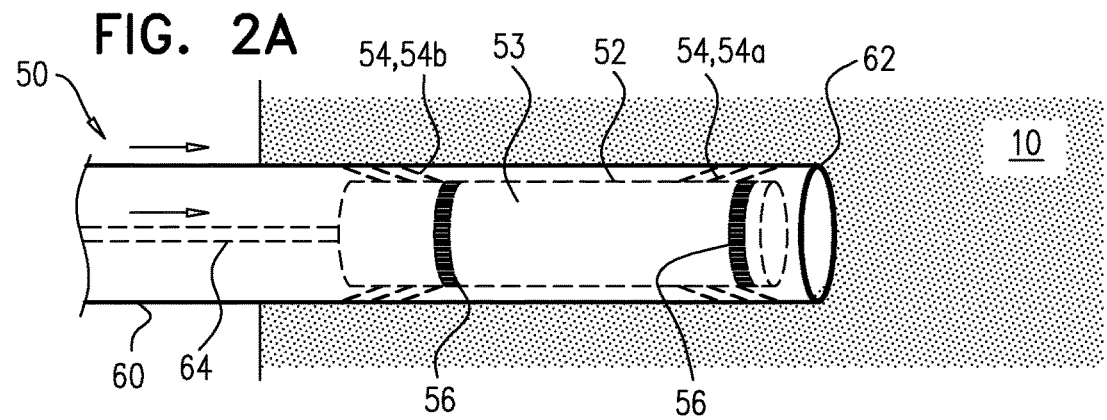
FIGS. 2A-G are schematic illustrations of a system comprising an implant, which comprises an implant body, at least one electrode, and one or more directionally-biased anchors, in accordance with some applications of the invention.
Figure 2B:
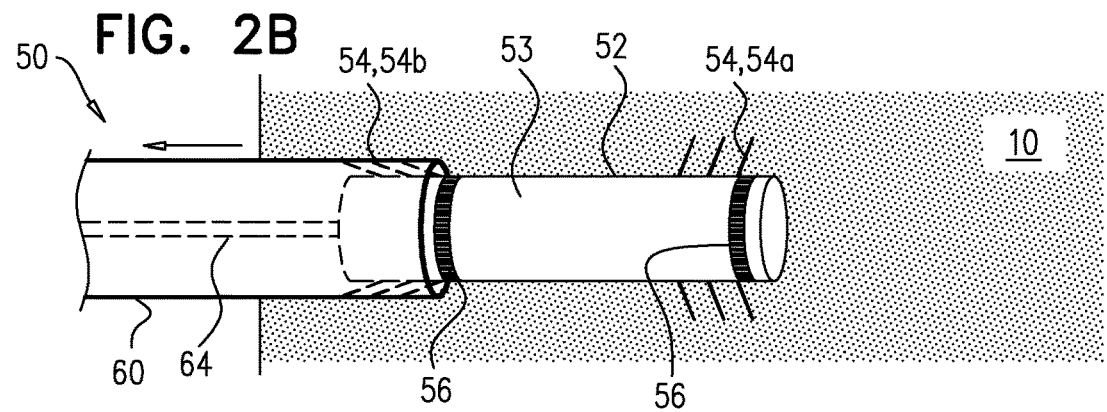
Figure 2C:
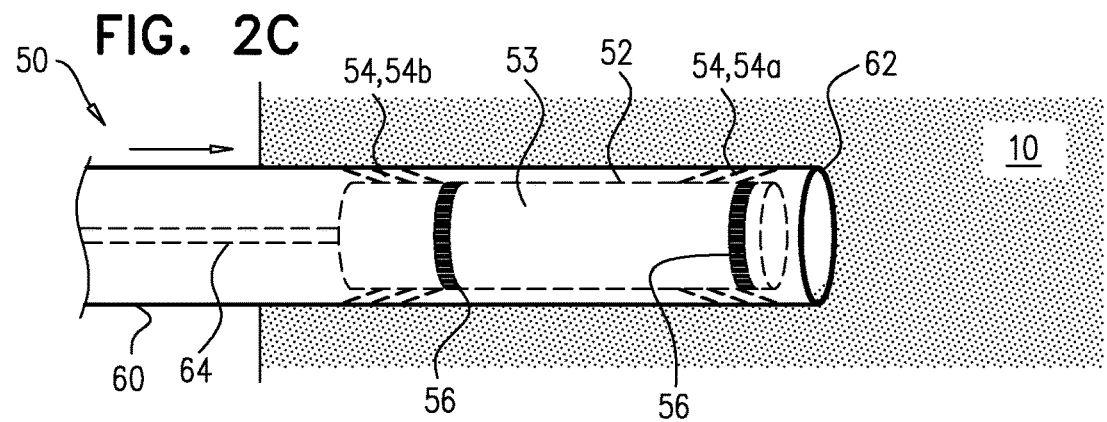
Figure 2D:
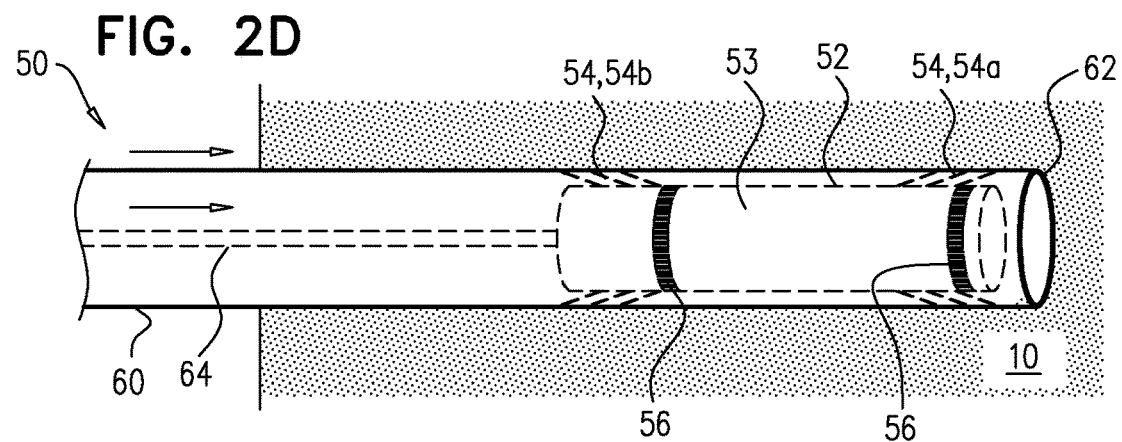
Figure 2E:
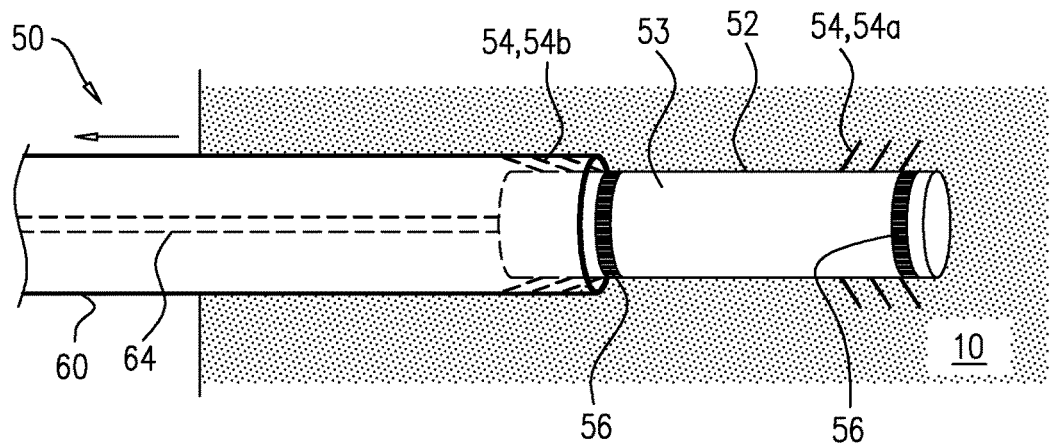
Figure 2F:
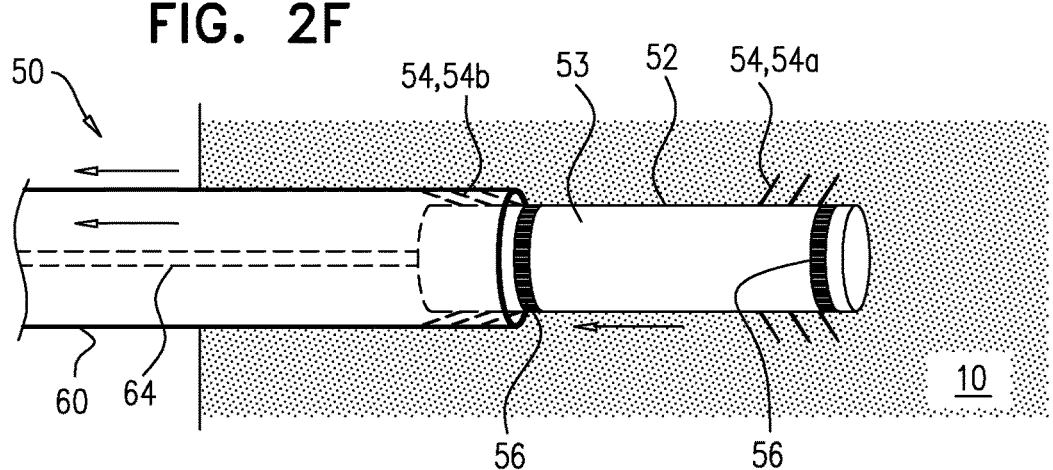
Figure 2G:
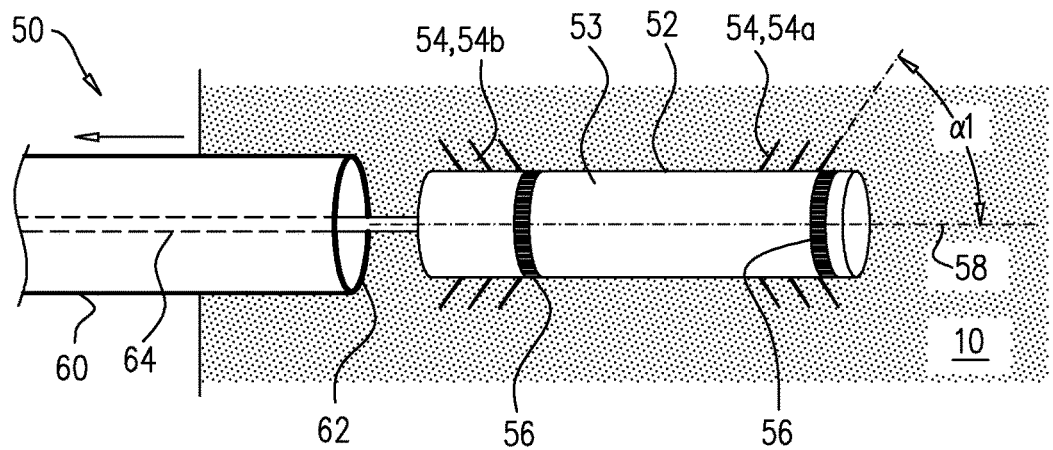

Typically, distal anchors 54b comprise at least one barb that protrudes, in the distal direction, at a nonzero angle alpha_1 with respect to a longitudinal axis 58 of the implant body (e.g., is deflected with respect to the longitudinal axis; shown in FIG. 2G). Similarly, proximal anchors 54a comprise at least one barb that protrudes, in the proximal direction, at a nonzero angle with respect to longitudinal axis 58. For some applications, and as shown with reference to FIGS. 2A-G, the barbs of anchors 54b protrude radially from the lateral surface of implant body 53. Typically, anchors 54 (e.g., anchors 54a and 54b) have a constrained state and an unconstrained state, angle alpha_1 being greater in the unconstrained state than in the constrained state. For some applications, and as shown with reference to FIGS. 2A-G, in the constrained state, the anchors are held against the lateral surface of implant body 53, and move away from the lateral surface when moving into the unconstrained state. Typically, system 50 further comprises an implant-storage member 60, shaped to define a space that is configured to house implant 52, and an opening 62 through which the implant is bidirectionally movable. System 50 also typically further comprises a delivery manipulator 64, configured to facilitate the bidirectional movement of implant 52 through opening 62.

FIG. 2A shows implant 52 having been delivered, within implant-storage member 60, to a first site within tissue 10. Implant-storage member 60 is then withdrawn proximally with respect to tissue 10 while implant 52 is held still with respect to the tissue, thereby exposing at least electrodes 56 of implant 52, from opening 62 (FIG. 2B). Implant 52 (e.g., electrodes 56 thereof) is driven to apply a current (e.g., a treatment current) to the tissue, and a response of a physiological parameter of the subject to the current is detected, e.g., as described hereinabove with respect to system 20, mutatis mutandis. If the response to the current is acceptable (e.g., greater than a threshold response), the implant may be deployed. Alternatively, as shown in FIG. 2C, member 60 may be advanced back over implant 52, and repositioned within tissue 10 (e.g., to a second site within the tissue, such as a deeper site), until an acceptable response is achieved. FIG. 2D shows member 60 and implant 52 at a second site within the tissue, and FIG. 2E shows implant 52, re-exposed from opening 62, in order to re-apply the current so as to test the second location.

It is to be noted that, for the "test" exposures shown in FIGS. 2B and 2E, distal anchors 54a, but not proximal anchors 54b, are exposed from opening 62. The angular disposition of anchors 54a with respect to implant body 53 facilitates the advancing of member 60 over implant 52, for repositioning within tissue 10. Furthermore, this angular disposition also facilitates proximal movement of implant 52 while the implant is in this state (e.g., with distal anchors 54a and electrodes 56 exposed). FIG. 2F shows such movement, which may be used for final adjustment (e.g., "fine tuning") of the position of the implant. For some applications, during such proximal movement, anchors 54a move at least slightly toward longitudinal axis 58.

Once a desired site has been established, implant 52 is deployed by withdrawing member 60 such that all of the implant, including proximal anchors 54b, are exposed from opening 62 (FIG. 2G). As described hereinabove, proximal anchors 54b inhibit proximal movement of the implant. This inhibition, in combination with that provided by anchors 54a, which inhibit distal movement of the implant, anchors the implant within tissue 10.

Figure 3:
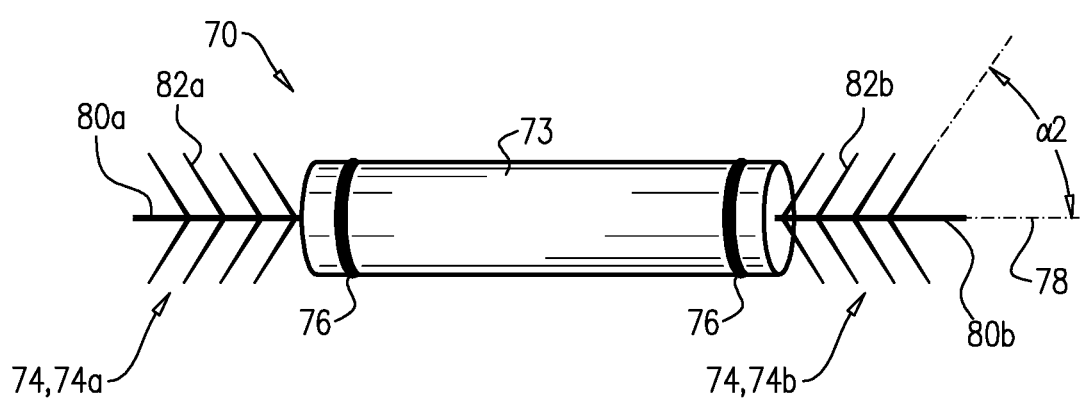
FIG. 3 is a schematic illustration of an implant comprising an implant body, at least one electrode, and one or more directionally-biased anchors, in accordance with some applications of the invention.

Reference is made to FIG. 3, which is a schematic illustration of an implant 70, comprising an implant body 73, at least one electrode 76, and one or more directionally-biased anchors 74, in accordance with some applications of the invention. Anchors 74 typically comprise one or more proximal anchors 74a and one or more distal anchors 74b. Distal anchors 74a are configured to inhibit movement of the implant (e.g., of implant body 53) through tissue 10, in a distal direction more than in a proximal direction. Similarly, proximal anchors 74b are configured to inhibit movement of the implant in a through the tissue, in the proximal direction more than in the distal direction.

Typically, distal anchors 74b comprise (1) a rod 80b that protrudes distally from implant body 73 on a longitudinal axis 78 of the implant, and (2) at least one barb 82b that protrudes, in the distal direction, at a nonzero angle alpha_2 with respect to the longitudinal axis (e.g., is deflected with respect to the longitudinal axis). Similarly, proximal anchors 74a comprise (1) a rod 80a that protrudes distally from implant body 73 on longitudinal axis 78 of the implant, and (2) at least one barb 82a that protrudes, in the proximal direction, at a nonzero angle with respect to the longitudinal axis.

For some applications, implant 70 is used in combination with apparatus and techniques described with reference to FIGS. 2A-G, mutatis mutandis.

Reference is again made to FIGS. 2A-G and 3. For some applications of the invention, the directionally-biased anchors, and/or the barbs thereof, crudely represent ears of wheat or barley.

Figure 4A:
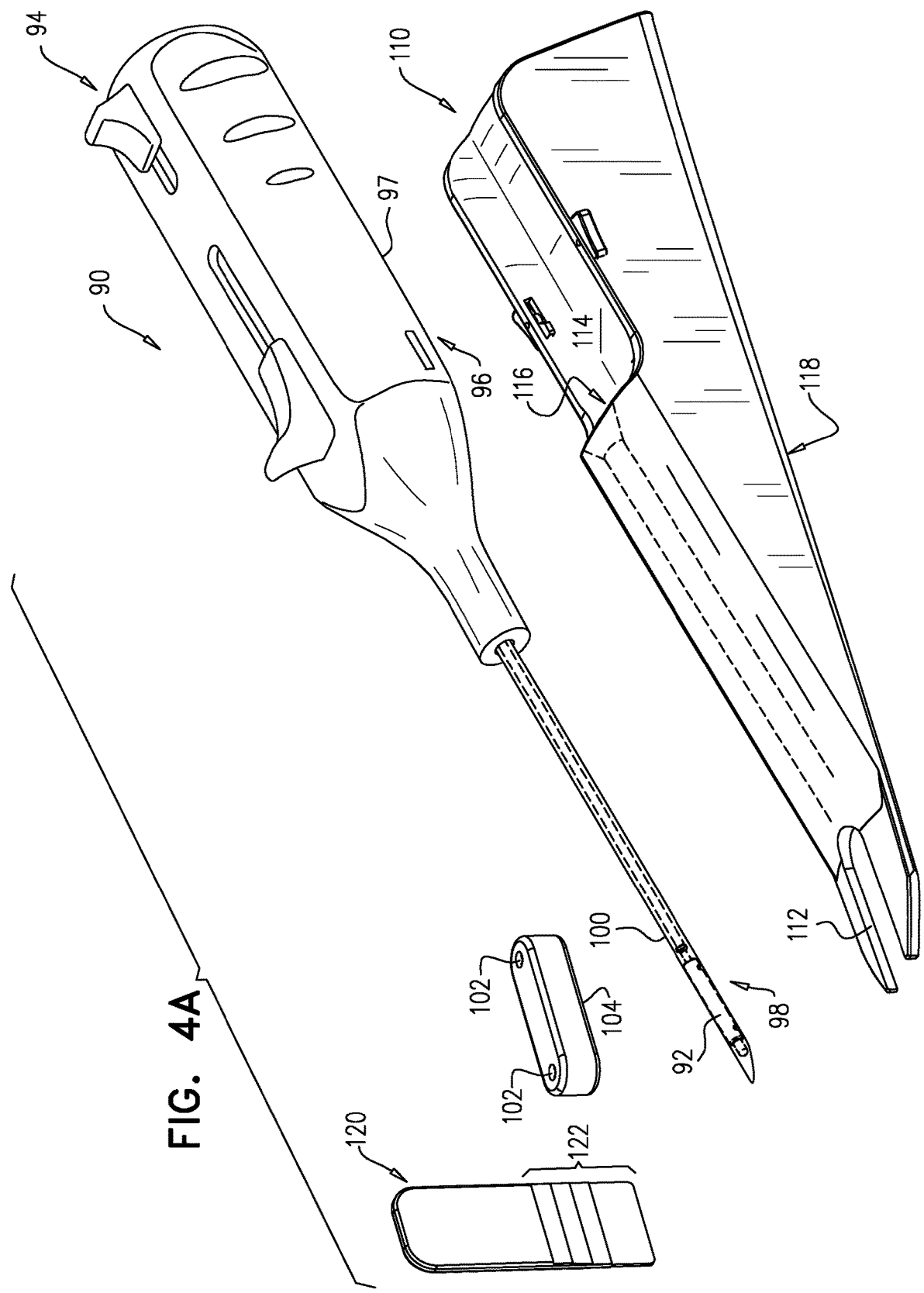

Reference is made to FIGS. 4A-H, which are schematic illustrations of a system 90, for facilitating percutaneous delivery of an implant 92 to a target site in the body of a subject, in accordance with some applications of the invention. For some applications, implant 92 comprises an implant described elsewhere herein, such as implant 20, implant 50, and/or implant 70. FIG. 4A shows the components of system 90. System 90 comprises a delivery tool 94, having a proximal portion 96 and a distal portion 98, the distal portion comprising an implant-storage member 100, configured to be percutaneously advanced toward the target site, and shaped to define a space that is configured to house the implant, and an opening through which the implant is advanceable. For some applications, implant-storage member 100 comprises an implant-storage member described elsewhere herein, such as implant-storage member 24 and/or implant-storage member 60. Typically, proximal portion 96 comprises a handle 97.

Figure 4B:
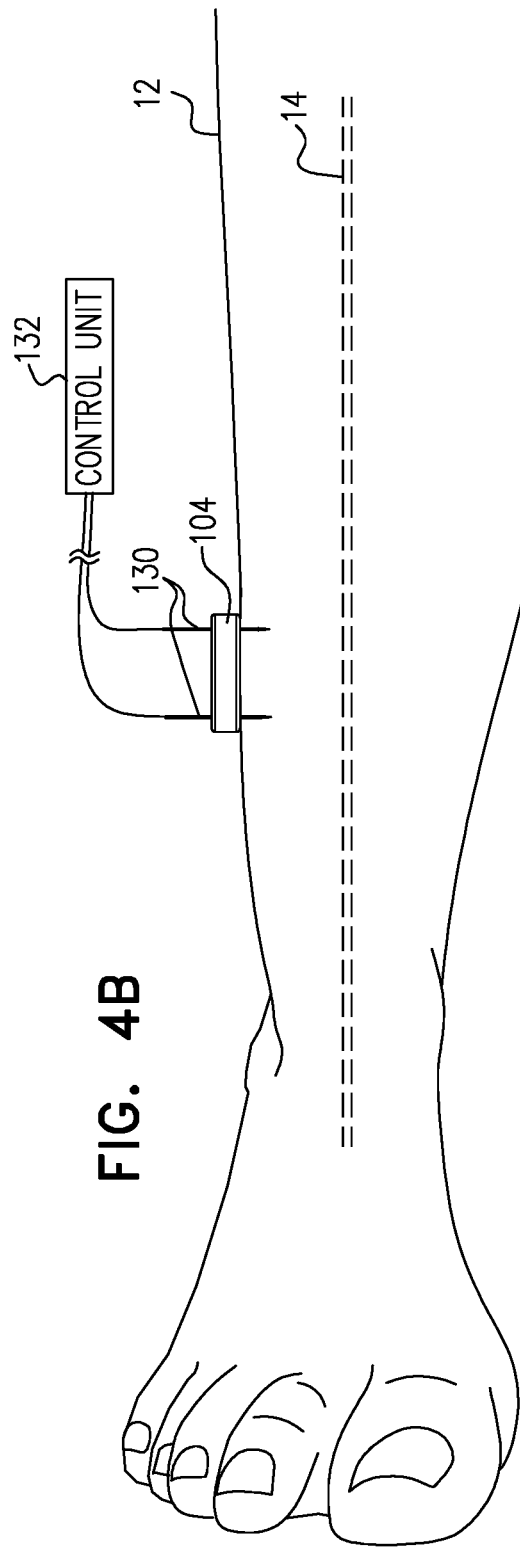

System 90 further comprises a guide 104, shaped to define one or more channels 102 that are configured to facilitate advancement of one or more respective transcutaneous electrodes, via a respective channel, through the skin of the subject, and to the target site. It is to be noted that throughout the present application, including the specification and the claims, the term "transcutaneous electrode" refers to an electrode that is configured to be placed through the skin of the subject while being coupled to extracorporeal apparatus, e.g., as shown in FIG. 4B, and that is typically placed temporarily. The term "transcutaneous electrode" is used so as to distinguish such an electrode from other electrodes described in the present application, such as an electrode that is a component of a percutaneously-implanted implant.

System 90 further comprises a mount 110, configured to be placed on the skin of the subject in a predetermined position with respect to channels 102, and to be coupled to the delivery tool so as to facilitate delivery of the implant-storage member (and thereby the implant) to the target site (e.g., the site to which the transcutaneous electrodes are advanced via channels 102). Typically, mount 110 is configured to be placed in a predetermined position with respect to guide 104 (e.g., to be coupled to guide 104 in the predetermined position). For example, and as shown in FIGS. 4A-H, mount 110 may be shaped to define a receptacle 112 within which at least a portion of guide 104 is placeable. For some applications, mount 110 comprises and/or is integral with guide 104, and/or itself defines channels 102.

Mount 110 is further configured to be coupled to delivery tool 94, such that the delivery tool (e.g., implant-storage member 100 thereof) is placed in a given position with respect to channels 102. For example, mount 110 may be shaped to define a cradle 114, configured to receive handle 97 of delivery tool 94, and/or a lumen 116, configured to receive distal portion 98 of the delivery tool. Cradle 114 and lumen 116 are disposed at a given angular disposition alpha_4 with respect to a skin-facing side (e.g., a skin-contacting surface 118) of mount 110. Typically, angle alpha_4 is less than 30 degrees and/or greater than 10 degrees (e.g., between 10 and 30 degrees).

System 90 typically further comprises a depth indicator 120, such as a gauge 122 (e.g., a plurality of graduated markings), configured to indicate a depth of insertion of the transcutaneous electrodes, as described in more detail hereinbelow.

FIGS. 4B-H show system 90 being used to facilitate implantation of implant 92, in accordance with some applications of the invention. It is to be noted that system 90 is shown being used to facilitate implantation of implant 92 in a leg 12 of the subject in a vicinity of a tibial nerve 14 of the subject, by way of illustration, and not by way of limitation. Guide 104 is placed on the skin of the subject, and transcutaneous electrodes 130 are advanced, through channels 102 of guide 104, through the skin of the subject, and into a tissue of the subject (FIG. 4B). Electrodes 130 are driven (e.g., by an extracorporeal control unit 132) to apply (e.g., to the tissue of the subject) a current that is similar (e.g., identical) to a current that implant 92 is configured to apply. Guide 104 and electrodes 130 may be repositioned multiple times until a target site is identified, such as a site at which the current has a maximal effect on a detected physiological parameter of the subject.

Figure 4C:
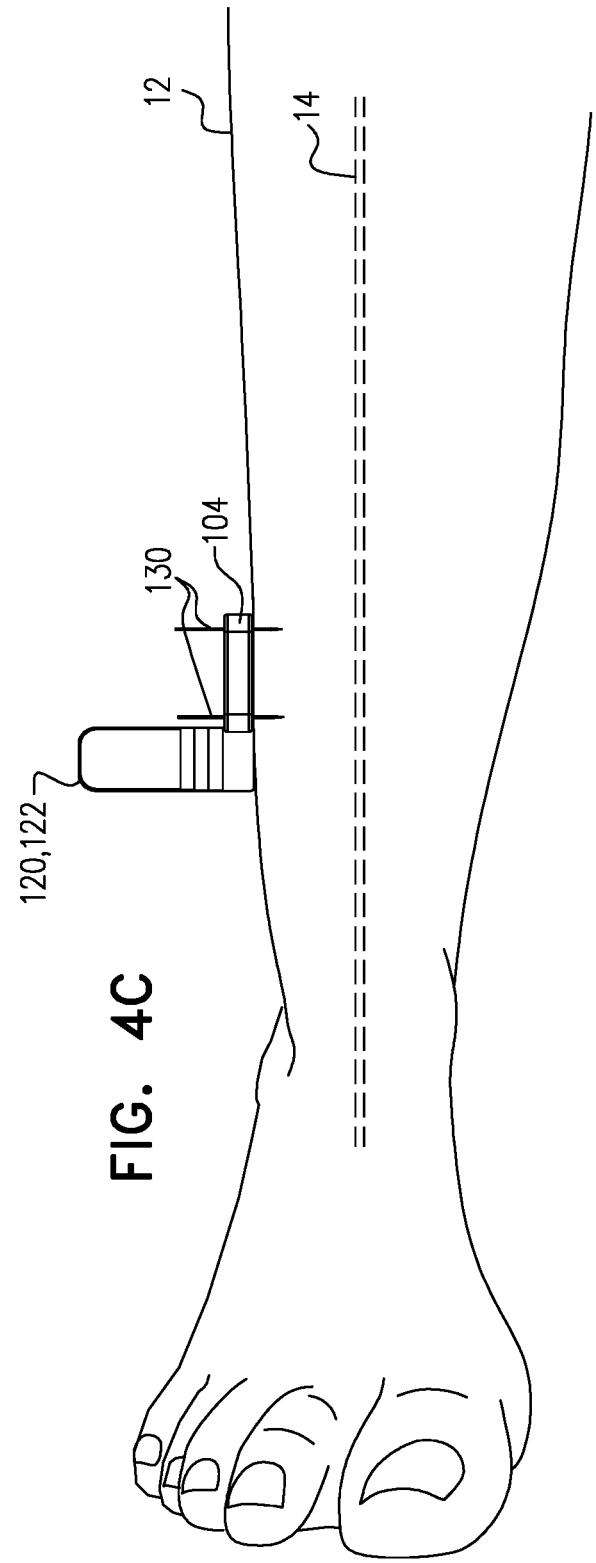

In addition to repositioning of guide 104 at different sites on the skin of the subject, electrodes 130 may be repositioned at different depths within the tissue of the subject. For some applications, the depth of the target site (e.g., the depth at which the electrodes provide maximal effect) is be determined using depth indicator 120. For example, gauge 122 may be placed next to electrodes 130, and the depth determined by observing the position of a part of the electrodes (e.g., a proximal end of the electrodes) with respect to graduated markings on the gauge (FIG. 4C). Alternatively or additionally, electrodes 130 may comprise gradated markings to indicate a depth of the electrodes within the tissue.

Subsequently, mount 110 is placed on the skin of the subject, in the given position with respect to guide 104, e.g., by placing at least a portion of guide 104 within receptacle 112 (FIG. 4D). For some applications, system 90 comprises a plurality of mounts 110, each mount being configured to hold delivery tool 94 at a different angular disposition with respect to the skin of the subject, such as by each respective cradle 114 and/or lumen 116 having a different angular disposition with respect to skin-contacting surface 118 of the mount. Alternatively, mount 110 (e.g., cradle 114 and/or lumen 116 thereof) may be adjustable. An operating physician selects one of the plurality of mounts, or adjusts the adjustable mount, according to the determined depth of the target site. For some applications, gauge 122 is color-coded, and each of the plurality of mounts 110 is colored respectively, to facilitate correct selection by the operating physician.

Subsequently, mount 110 is secured to the skin (e.g., using adhesive tape 128), and delivery tool 94 is coupled to the mount, such as by (1) sliding the distal portion of the delivery tool, comprising implant-storage member 100, through the lumen of the mount and into the tissue of the subject, and (2) coupling handle 97 of the delivery tool to the cradle of the mount (FIG. 4E). The positioning of mount 110 with respect to guide 104, and the coupling of the delivery tool to the mount (and, optionally, the selection and/or adjustment of the mount in response to determining the depth of transcutaneous electrodes 130), facilitate the positioning of member 100, housing implant 92, at the target site that was previously determined using the transcutaneous electrodes.

Figure 4H:
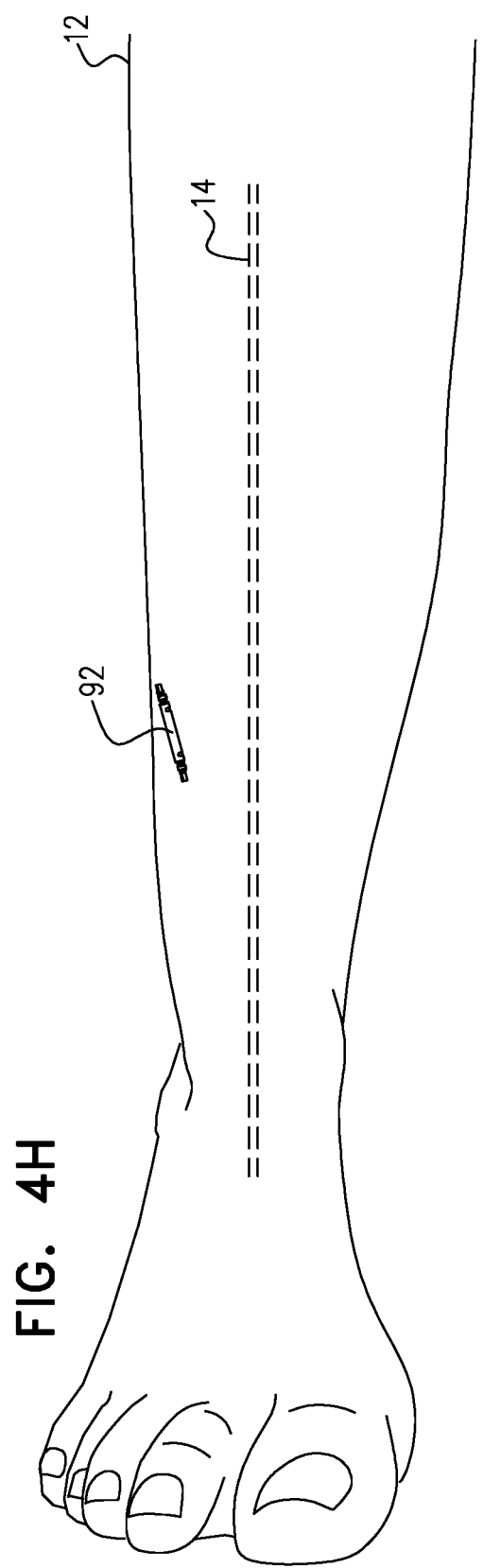

Implant 92 is subsequently deployed by withdrawing implant-storage member 100 proximally while the implant is held still with respect to the tissue, thereby leaving the implant exposed at the target site (FIG. 4F). For some applications, tool 94 comprises a delivery manipulator 134 (typically similar to delivery manipulators 34 and/or 64 described hereinabove with respect to FIGS. 1A-D and 2A-G, respectively), which holds implant 92 in place in this manner. For such applications, the delivery manipulator is subsequently decoupled from implant 92 (FIG. 4G). System 90 is subsequently removed from the subject, leaving implant 92 at the target site (FIG. 4H).

Reference is made to FIGS. 5A-M, which are schematic illustrations of a system 150 for facilitating percutaneous delivery of an implant 170, the system comprising a rigid delivery tube 152 and at least a first flexible longitudinal member, slidably coupled to the delivery tube, in accordance with some applications of the invention. The first flexible longitudinal member is configured such that a distal portion thereof has a tendency to be disposed at a nonzero angle with respect to a proximal portion thereof, such that a distal tip of the first flexible longitudinal member (e.g., a distal tip of the distal portion thereof) is disposed at a nonzero angle with respect to the proximal portion of the first flexible longitudinal member. That is, the first flexible longitudinal member is configured such that the distal portion and/or distal tip thereof have a tendency to be deflected with respect to the proximal portion thereof. For example, the first flexible longitudinal member may have shape memory, e.g., may comprise a shape memory material such as nitinol. Typically, the first flexible longitudinal member comprises a flexible tube 154, having a distal portion 158 and a distal tip 159, and system 150 further comprises a second flexible longitudinal member, typically comprising a wire 156, slidable through tube 154. For some applications, wire 156 also comprises a shape memory material such as nitinol. Typically, tube 154 and/or wire 156 are configured to pierce tissue of the subject. For example, tube 154 and/or wire 156 may each have a sharp distal tip and/or may be sufficiently rigid that a pushing force applied to the proximal end can drive the tube and/or wire through the tissue.

For some applications, (1) implant 170 comprises and/or is similar to another implant described herein, such as implant 22, implant 52, implant 70, implant 92, implant 180 or implant 206, mutatis mutandis, and/or (2) system 150 may be used to facilitate implantation of these other implants. Typically, system 150 comprises a mount 160, configured to be placed on the skin of the subject, rigid delivery tube 152, flexible tube 154 and wire 156 being slidably coupled to the mount. Typically, flexible tube 154 is disposed and slidable within delivery tube 152, and wire 156 is disposed and slidable within flexible tube 154.

System 150 has at least one retracted configuration in which distal portion 158 of tube 154 is disposed within (e.g., retracted into) tube 152, and is thereby held straight by tube 152, such that the distal portion and/or distal tip 159 is generally parallel with the longitudinal axis of tube 152 (e.g., to be coaxial with tube 152). FIGS. 5A-B show system 150 in a first, withdrawn retracted configuration (described in more detail hereinbelow), and FIG. 5J shows system 150 in a second, advanced retracted configuration (described in more detail hereinbelow), in which the tube 152 and tube 154 are disposed further from mount 160 than when the system is in the withdrawn retracted configuration. System 150 has an extended configuration (FIGS. 5C-D, described in more detail hereinbelow) in which distal portion 158 of tube 154 is disposed outside of tube 152 (e.g., distal to the distal end of tube 152), and due to the shape memory, is disposed at a nonzero angle with respect to longitudinal axis 153 of tube 152, such that distal tip 159 of tube 154 is disposed at a nonzero angle alpha_3 with respect to longitudinal axis 153 (FIG. 5C).

It is to be noted that system 150 is shown being used to facilitate implantation of implant 170 in leg 12 of the subject in a vicinity of tibial nerve 14 of the subject, by way of illustration, and not by way of limitation. For example, system 150 may be used at other sites of the subject, such as to implant the implant in a vicinity of another tissue, such as another nerve of the subject.

Mount 160 is placed on leg 12 of the subject such that a skin-facing side (e.g., a skin-contacting surface 161) of the mount is in contact with the skin of the subject, typically while system 150 is in the withdrawn retracted configuration (FIGS. 5A-B). Tube 152 is disposed at an angle alpha_5 with respect to a plane defined by skin-contacting surface 161. Angle alpha_5 is typically greater than 30 degrees and/or less than 45 degrees (e.g., between 30 and 45 degrees).

FIGS. 5A-B show tube 152 (e.g., a distal end thereof) protruding out of mount 160 (e.g., past skin-contacting surface 161 thereof) and penetrating the skin of leg 12. Typically, mount 160 is placed (e.g., secured) on the skin while tube 152 does not protrude in this manner, and tube 152 is subsequently advanced through the skin. For example, tube 152 (e.g., a distal end thereof) may be disposed within mount 160 while the mount is placed on the skin, or may be introduced into the mount subsequently to the placement of the mount on the skin. Alternatively, mount 160 is placed (e.g., secured) on the skin while tube 152 protrudes past skin-contacting surface 161. For some applications, tube 152 (e.g., the distal end thereof) does not protrude from mount 160 (e.g., does not penetrate the skin) until the step described with reference to FIG. 5G.

For some applications, system 150 is used in combination with apparatus and/or methods described hereinabove with reference to FIGS. 4A-H, so as to facilitate delivery of implant 170 to a target site. For example, guide 104, described hereinabove as a component of system 90, may be previously placed on the skin to provide channels for transcutaneous electrodes for identifying the target site, and as shown with reference to FIGS. 5A-M, subsequently used to facilitate placement of mount 160, as described hereinabove with reference to FIGS. 4A-H, mutatis mutandis. Similarly, mount 160 may be secured to the skin using adhesive tape 128 (not shown in FIGS. 5A-M).

Subsequently, flexible tube 154 is extended out of tube 152, thereby moving system 150 into the extended configuration thereof (FIGS. 5C-D). As described hereinabove, due to shape memory, a distal portion 158 of tube 154 responsively bends such that distal tip 159 of tube 154 is disposed at nonzero angle alpha_3 with respect to longitudinal axis 153 of tube 152.

Figure 5E:
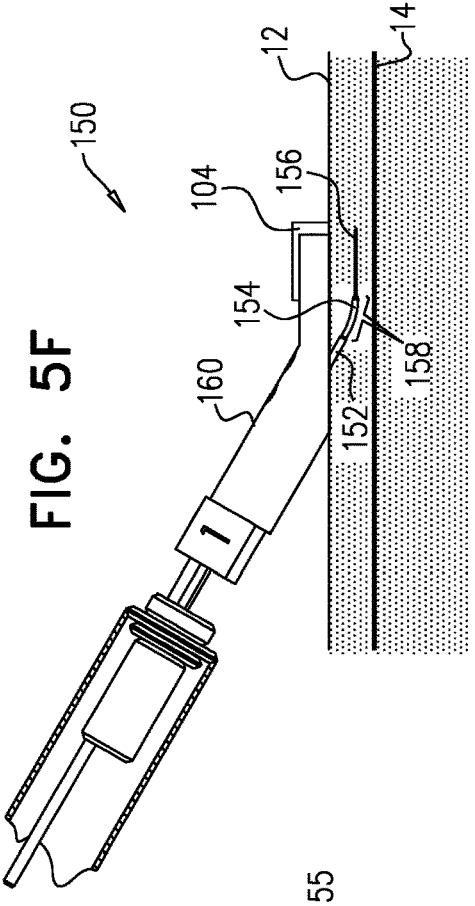

Typically, the angle at which distal portion 158 (e.g., distal tip 159) of tube 154 is disposed with respect to the plane of the skin of the subject, and with respect to tibial nerve 14, is shallower than that at which tube 152 is disposed with respect to the plane of the skin of the subject, and with respect to tibial nerve 14. For example, a longitudinal axis 155 of distal portion 158 (e.g., of distal tip 159) may be disposed at less than 20 degrees, such as less than 10 degrees, e.g., less than 5 degrees, to the skin and/or to the tibial nerve. For some applications, and as shown in FIG. 5E, axis 155 is generally parallel with tibial nerve 14. Typically, and as shown in FIG. 5E, system 150 (e.g., tube 154) is configured such that, in the extended configuration, portion 158 is disposed, with respect to the plane defined by skin-contacting surface 161, at a shallower angle than is tube 152 (e.g., portion 158 is substantially parallel to the plane defined by surface 161).

Figure 5F:
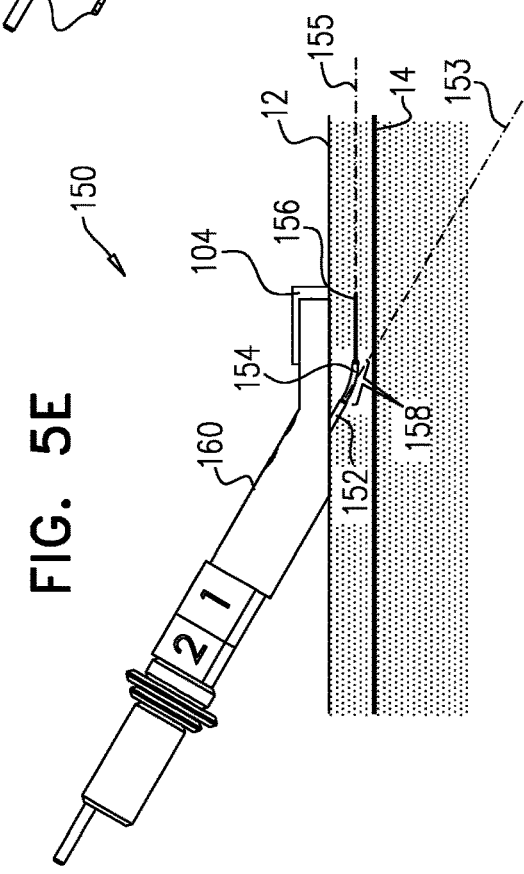

For applications in which system 150 comprises wire 156, wire 156 is subsequently advanced through tube 154, and further into the tissue (FIGS. 5E-F). For some applications, wire 156 moves further along axis 155. For some applications, wire 156 has shape memory, and a distal end of the wire is disposed at a nonzero angle with respect to axis 155.

Figure 5G:
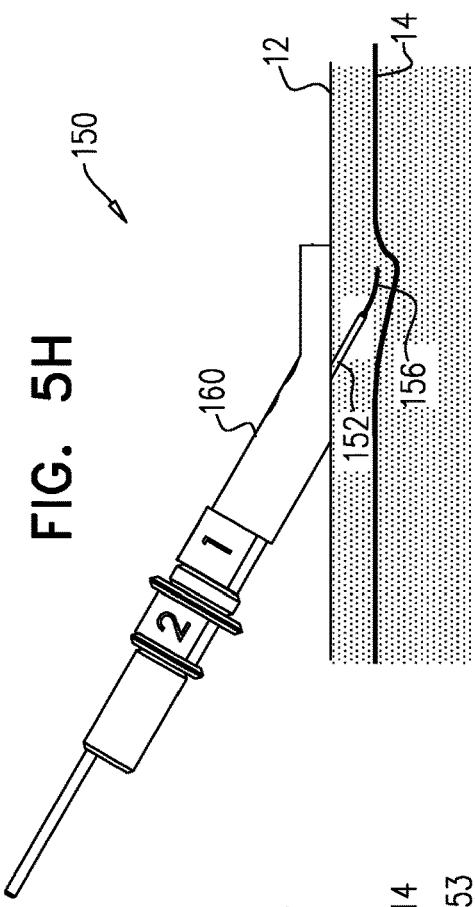
Figure 5H:
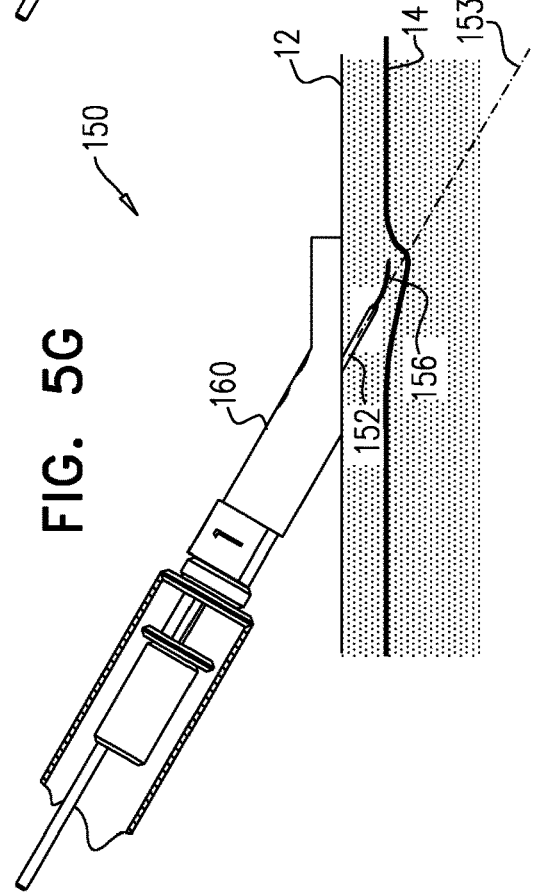

Rigid delivery tube 152 is advanced distally, thereby moving system 150 into the advanced retracted configuration (FIGS. 5G-J). FIGS. 5G-I show tube 152 having been advanced over tube 154, and FIG. 5J shows tube 152 having been advanced further, over wire 156. For some applications, system 150 only comprises one flexible longitudinal member, and tube 152 is advanced over the one flexible longitudinal member. As tube 152 is advanced, tube 154 and wire 156 are straightened, and the tissue in the vicinity of the tube and wire is distorted responsively. As shown in FIGS. 5G-J, this distortion may include distortion (e.g., bending, pressing, and lifting), of skin, subcutaneous tissue, and tibial nerve 14. For some applications, this bending maintains the shallow angle between nerve 14, and wire 156 (and distal end 158 of tube 152) as wire 156 (and distal end 158) are brought into alignment with longitudinal axis 153 of tube 152. That is, the bending of nerve 14 brings a longitudinal axis 163 of a portion of nerve 14 into closer alignment with axis 153 (e.g., parallel to axis 153). For some applications, the flexible longitudinal member (e.g., tube 154 and/or wire 156) thereby acts as an anchor that draws progressive portions of tissue toward axis 163 as tube 152 is advanced over progressive portions of the flexible longitudinal member.

For some applications in which guide 104 is used to facilitate placement of mount 160, the guide is removed from the skin once the mount has been placed on (e.g., and secured to) the skin of the subject. FIG. 5G shows guide 104 having been removed after the step illustrated in FIG. 5F and the step illustrated in FIG. 5H. However, it is to be understood that guide 104 may be removed at another stage in the procedure, or may be left in place until the end of the procedure.

Subsequently, tube 154 and wire 156 are removed from the tissue (e.g., by removing the tube and wire from mount 160), leaving the distal end of rigid delivery tube 152 disposed in the tissue (FIG. 5K). Implant 170 is subsequently delivered, via tube 152, to the tissue (FIG. 5L). For example, a delivery manipulator 168, reversibly coupled to implant 170, may be advanced through delivery tube 152. For some applications, delivery manipulator 168 comprises and/or is similar to another delivery manipulator described herein, such as delivery manipulators 34, 64, and 134. Due to the angle at which tube 152 is disposed, implant 170 is thereby delivered at a shallow angle with respect to nerve 14 (e.g., generally parallel with nerve 14). For some applications, implant 170 comprises a plurality of electrodes (e.g., as described hereinabove for implant 22, mutatis mutandis) and positioning of the implant at this shallow angle with respect to nerve 14 results in positioning of each of the electrodes at a similar distance (e.g., the same distance) from the nerve. Delivery tube 152 and the remainder of system 150 are then removed from the body of the subject. Removal of delivery tube 152 allows the tissue to return to its original state (e.g., allows nerve 14 to straighten), implant 170 remaining in its angular disposition with respect to the tissue (e.g., with a longitudinal axis of the implant generally parallel with nerve 14), as shown in FIG. 5M.

Figure 6A:
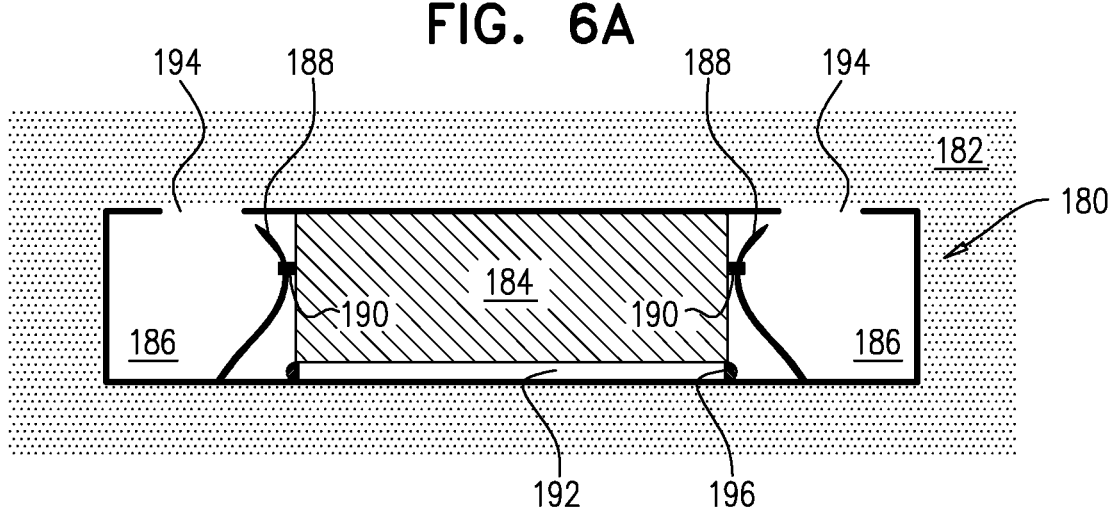
FIGS. 6A-C are schematic illustrations of an implant configured to be percutaneously implanted in a tissue of a subject, in accordance with some applications of the invention.
Figure 6B:
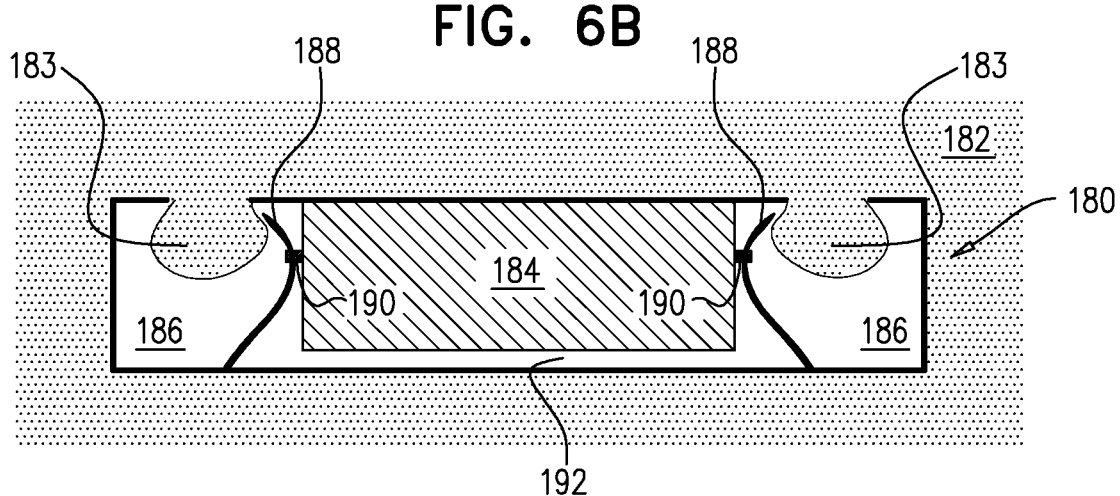
Figure 6C:
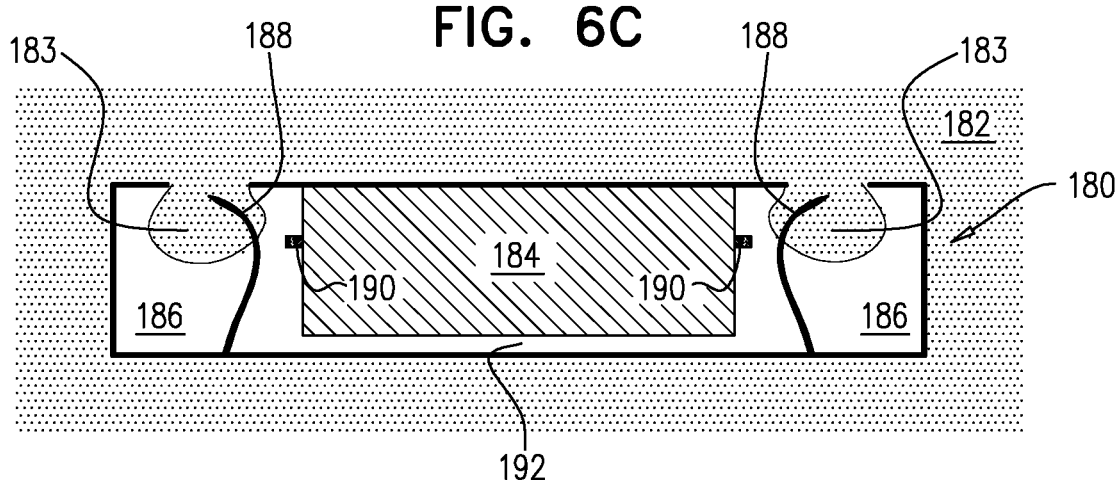

Reference is made to FIGS. 6A-C, which are schematic illustrations of an implant 180 configured to be percutaneously implanted in a tissue 182 of a subject, in accordance with some applications of the invention. Implant 180 comprises an implant body 184, typically comprising a control unit and/or circuitry, one or more (e.g., two) suction chambers 186, and one or more (e.g., two) anchors 188, disposed within a respective suction chamber. Each suction chamber is shaped to define a window 194, and each anchor has a first state and a second state, and is configured such that, when transitioning from the first state to the second state, a tissue-piercing element of the anchor moves with respect to the window of the respective suction chamber (e.g., past, or past at least part of the window). For some applications, and as shown in FIGS. 6A-C, implant 180 comprises a vacuum source 192, which is provided closed, and is configured to be placed in fluid communication with suction chambers 186, so as to draw at least a partial vacuum into the suction chambers. Alternatively, implant 180 may be configured to be connected to an external (e.g., extracorporeal) vacuum source such that the vacuum source is in fluid communication with the suction chambers.

FIG. 6A shows implant 180 having been delivered into tissue 182 of the subject. Vacuum source 192 is not in fluid communication with suction chambers 186. For example, a valve 196 may be disposed between the vacuum source and each suction chamber, and may be closed. Anchors 188 are in the first state thereof. For example, each anchor may be constrained in the first state (e.g., a constrained state) thereof by a respective constraining member 190.

Subsequently, vacuum source 192 is placed in fluid communication so as to draw at least a partial vacuum is drawn into suction chambers 186, such as by opening valves 196 (FIG. 6B). The at least partial vacuum draws (e.g., sucks) a portion of tissue 182, via windows 194, into chambers 186, the tissue forming a bulge 183 of tissue within each chamber, in the vicinity of each window.

Subsequently, anchors 188 transition into the second state thereof (FIG. 6C). For example, constraining members 190 may release anchors 188, the anchors being configured to automatically transition toward the second state (e.g., an unconstrained state) when released. For example, anchors 188 may comprise a spring and/or a shape memory material such as nitinol. As described hereinabove, each anchor is configured such that, when transitioning from the first state to the second state, a tissue-piercing element of the anchor moves with respect to (e.g., past) the window of the respective suction chamber. When a bulge 183 is disposed within each chamber in a vicinity of each window, the tissue-piercing element of each anchor thereby pierces the bulge of tissue, thereby anchoring implant 180 to the tissue.

It is hypothesized that anchors 188, which are disposed within suction chambers 186, reduce a likelihood of inadvertently damaging tissue of the subject, compared with anchors that are disposed on the outside of an implant. For some applications, the at least partial vacuum drawn into suction chambers 186 only lasts for a short duration (e.g., less than an hour, such as less than a minute, such as for a few seconds), and dissipates subsequent to the anchoring of anchors 188 to bulges 183.

Reference is made to FIGS. 7A-B, which are schematic illustrations of a system 200 for use with a nerve 202 of a subject, in accordance with respective applications of the invention. System 200 comprises one or more helical electrodes 204 (e.g., a first helical electrode 204a and a second helical electrode 204b), configured to be wrapped around respective sites on nerve 202, an injectable implant 206, configured to be percutaneously implanted in a vicinity of nerve 202, one or more wires 208 (e.g., a first wire 208a and a second wire 208b), coupling respective helical electrodes to the injectable implant, and a helical anchor 210, configured to be wrapped around another site on nerve 202, and comprising a brace 212, configured to be coupled to a portion of each wire 208 that is disposed between helical electrodes 204 and the injectable implant. Anchor 210 and brace 212 are hypothesized to reduce mechanical forces between implant 206 and electrodes 204. Furthermore, implant 206 is typically implanted close to electrodes 204, so as to reduce movement of the implant with respect to the electrodes caused by movement of parts of the body (e.g., limbs) of the subject, thereby further reducing mechanical forces between the implant and the electrodes.

System 200 comprises an antenna 214, configured to wirelessly receive energy, the implant being configured to receive the received energy from the antenna. In the application of the invention shown in FIG. 7A, implant 206 comprises antenna 214. In the application of the invention shown in FIG. 7B, anchor 210 comprises antenna 214, which is wiredly coupled via a third wire 208c to implant 206.

Figure 8B:
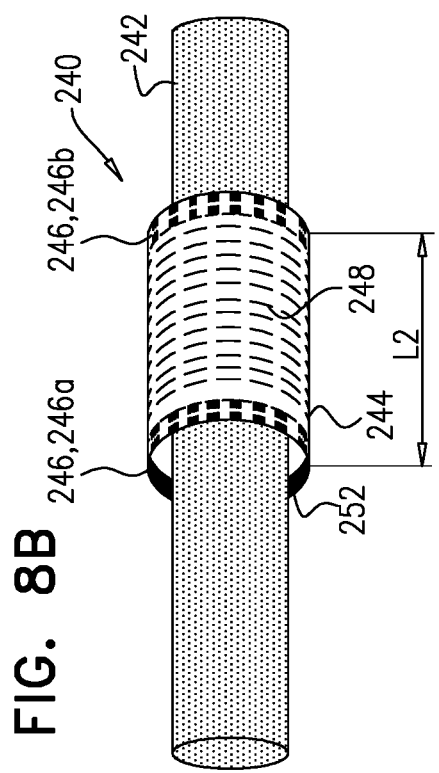
FIGS. 8A-C are schematic illustrations of a system for use with a nerve of a subject, in accordance with some applications of the invention.
Figure 8C:
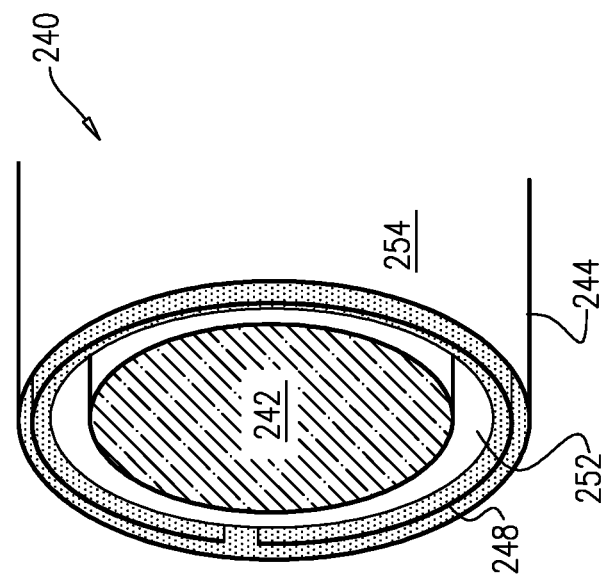
Figure 8A:
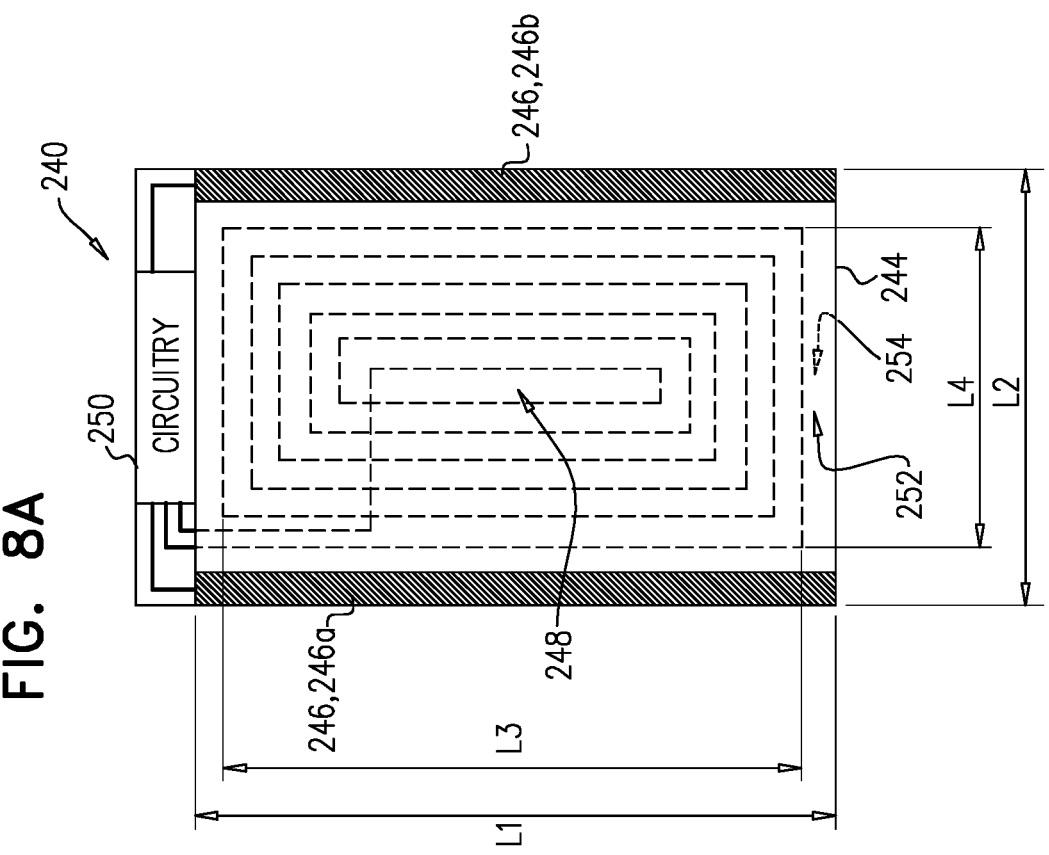

Reference is made to FIGS. 8A-C, which are schematic illustrations of a system 240 for use with a nerve 242 of a subject, in accordance with some applications of the invention. System 240 comprises (1) a cuff body 244, that comprises one or more electrodes 246 (e.g., a first electrode 246a and a second electrode 246b) and at least one planar antenna 248, configured to wirelessly receive energy, and (2) circuitry 250, configured to use the received energy from the planar antenna to drive electrodes 246 to apply a current to nerve 242.

Cuff body 244 has a first length L1 and a second length L2, lengths L1 and L2 being mutually orthogonal. FIG. 8A shows system 240 with cuff body 244 in an unrolled state in which the cuff body lies on a plane, and lengths L1 and L2 define an area of the cuff body on the plane. As shown, planar antenna 248 is disposed parallel with the plane of the cuff body. Typically, antenna 248 is disposed within the material of the cuff body, and is hence represented by dotted lines. Electrodes 246 are typically disposed on a first face 252 of the cuff body, the cuff body also having a second face 254, and a thickness between the first face and the second face. Typically, electrodes 246a and 246, are disposed at opposite ends of length L2 from each other, and typically have respective longest dimensions that are parallel to length L1.

Antenna 248 spans an area defined by a first length L3 and a second length L4 of the antenna, lengths L3 and L4 being mutually orthogonal. That is, antenna 248 defines spaces between a material from which it is formed (e.g., a wire), but as a whole, spans an area defined by lengths L3 and L4. Typically, antenna 248 spans an area that is at least 70 percent as great as the total area of the cuff body (defined by lengths L1 and L2).

It is to be noted that throughout this application, including the specification and the claims, the dimensions of planar antennas, including the terms "span" and "area", refers to such an overall dimension (e.g., an overall span and overall area) of the antenna. For some applications, and as shown in FIG. 8A, antenna 248 is shaped to generally define a rectangular spiral, having mutually orthogonal lengths L3 and L4, which define an area that the antenna spans.

FIG. 8B shows system 240 with cuff body 244 wrapped around nerve 242, such that first face 252 and electrodes 246 face the nerve. It is to be noted that length L2 of cuff body 244 defines a length of nerve 242 that is covered by the cuff body. FIG. 8C shows a cross-section through nerve 242 and cuff body 244, showing antenna 248 disposed within the material of cuff body 244.

Cuff body 244 defines a tube, first face 252 defining a 360-degree circumferential wall of the tube. Antenna 248 (e.g., the area thereof) extends at least 180 degrees around the circumferential wall. That is, length L3 extends at least 180 degrees around the circumferential wall. Antenna 248 may extend at least 270 degrees, such as at least 330 degrees, e.g., at least 360 degrees around the circumferential wall. For example, antenna 248 may circumscribe the circumferential wall.

Reference is made to FIGS. 9A-C, which are schematic illustrations of a system 260 for use with nerve 242, in accordance with some applications of the invention. As described hereinabove, cuff body 244 of system 240 comprises at least one planar antenna 248. FIGS. 8A-C show system 240 comprising exactly one planar antenna 248. System 260 is identical to system 240, except that, instead of planar antenna 248, system 260 comprises three planar antennas 268 (planar antenna 268a, planar antenna 268b, and planar antenna 268c).

FIG. 9A shows system 260 with cuff body 244 in an unrolled state in which the cuff body lies on a plane, and lengths L1 and L2 define an area of the cuff body on the plane. FIG. 9B shows a cross-sectional view of system 260 with cuff body 244 wrapped around nerve 242, such that first face 252 and electrodes 246 face the nerve. FIG. 9C is a simplified cross-sectional view, showing the position of the antennas of cuff body 244 around nerve 242.

Each planar antenna of system 260 spans about 120 degrees around the circumferential wall defined by first face 252 of cuff body 244. For example, respective lengths L3a, L3b, and L3c of planar antennas 268a, 268b, and 268c, each span about one third of length L1 of cuff body 244. Typically, a sum of the areas spanned by antennas 268a, 268b, and 268c is greater than the total area of the cuff body (defined by lengths L1 and L2). For example, the antennas may partly overlap each other.

Reference is again made to FIGS. 8A-9C. It is to be noted that the gaps between the antennas shown in FIGS. 8A-9C are for clarity, and that the gaps between the antennas may in fact be very small, such as practically non-existent. For some applications, such as described hereinbelow with respect to FIGS. 10-14, mutatis mutandis, antennas may overlap with each other.

Reference is made to FIGS. 10-14, which are schematic illustrations of planar antenna configurations for systems such as system 240 and/or system 260, in accordance with respective applications of the invention.

FIG. 10 shows planar antennas 278a and 278b, which are typically components of a system 270 that is identical, except for the antenna configuration thereof, to system 240 and/or system 260, described hereinabove. Planar antennas 278a and 278b each span 180 degrees around the circumferential wall defined by first face 252 of cuff body 244, and are typically rotationally offset with respect to each other such that (1) a first arc region 272a of cuff body 244 comprises overlapping portions of both antennas, (2), a second arc region 272b of the cuff body, disposed exactly opposite the first arc region, comprises no portions of an antenna, and (3) two arc regions 272c and 272d, disposed rotationally between the first and second arc regions, each comprise portions of only one antenna. For some applications, and as shown with reference to FIG. 10, planar antennas 278a and 278b are rotationally offset by 90 degrees with respect to each other, such that each arc region spans 90 degrees around the circumferential wall defined by first face 252. It is to be noted that any line that passes through the transverse cross-sectional center of system 270 passes through exactly two antennas. Planar antennas 278a and 278b may be alternatively be offset by another number of degrees with respect to each other, such as less than and/or greater than 90 degrees.

FIG. 11 shows planar antennas 288a, 288b, and 288c, which are typically components of a system 280 that is identical, except for the antenna configuration thereof, to system 240 and/or system 260, described hereinabove. Planar antennas 288a, 288b, and 288c each span 180 degrees around the circumferential wall defined by first face 252 of cuff body 244, and are typically rotationally offset with respect to each other such that (1) three first arc regions 282a of cuff body 244 each comprise overlapping portions of two antennas, and (2) three second arc regions 282b of the cuff body, each disposed exactly opposite a respective first arc region 282a, each comprise a portion of one antenna. For some applications, and as shown with reference to FIG. 11, planar antennas 288a and 288b are rotationally offset by 90 degrees with respect to each other, and planar antennas 288b and 288c are rotationally offset by 45 degrees with respect to each other, such that (1) one of each type of arc region (i.e., one region 282a and one region 282b) spans 45 degrees around the circumferential wall defined by first face 252, and (2) two of each type of arc region span 45 degrees around the circumferential wall. It is to be noted that any line that passes through the transverse cross-sectional center of system 280 passes through exactly three antennas. It is also to be noted that at no arc region of the cuff body do more than two antennas overlap. Planar antennas 288a, 288b, and 288c may be alternatively be offset by another number of degrees with respect to each other.

Figure 12:
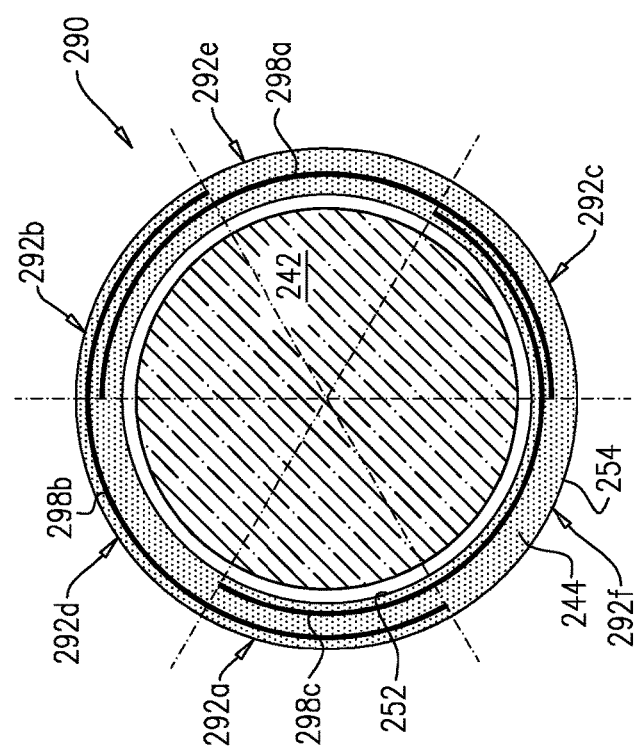

FIG. 12 shows planar antennas 298a, 298b and 298c, which are typically components of a system 290 that is identical, except for the antenna configuration thereof, to system 240 and/or system 260, described hereinabove. Planar antennas 298a, 298b, and 298c each span 180 degrees around the circumferential wall defined by first face 252 of cuff body 244, and are typically rotationally offset with respect to each other such that (1) three first arc regions 292a, 292b, and 292c of cuff body 244 comprises overlapping portions of two antennas, and (2) three second arc regions 292d, 292e, and 292f of the cuff body, each disposed exactly opposite a respective first arc region, each comprise portions of one antenna. For some applications, and as shown with reference to FIG. 12, planar antennas 298a, 298b, and 298c are rotationally offset by 120 degrees with respect to each other, such that each arc region spans 60 degrees around the circumferential wall defined by first face 252. It is to be noted that any line that passes through the transverse cross-sectional center of system 290 passes through exactly three antennas. It is also to be noted that at no arc region of the cuff body do more than two antennas overlap. Planar antennas 278a and 278b may alternatively be offset by another number of 180 degrees with respect to each other.

Figure 13:
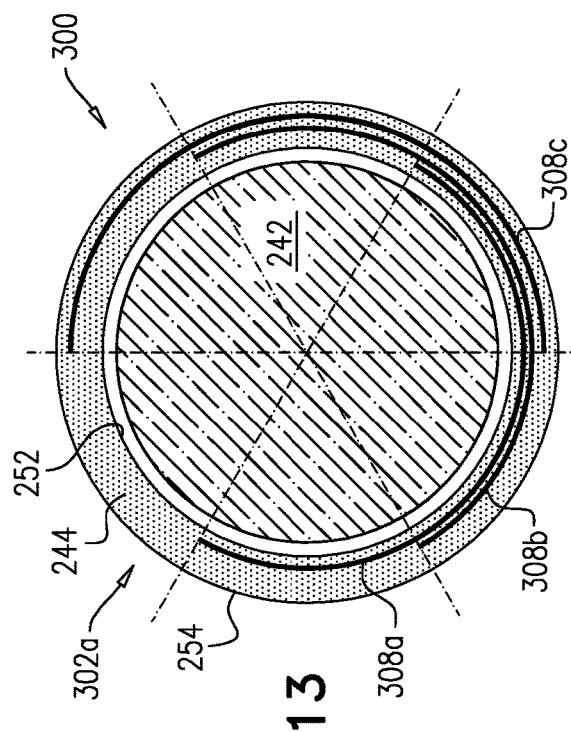
Figure 14:
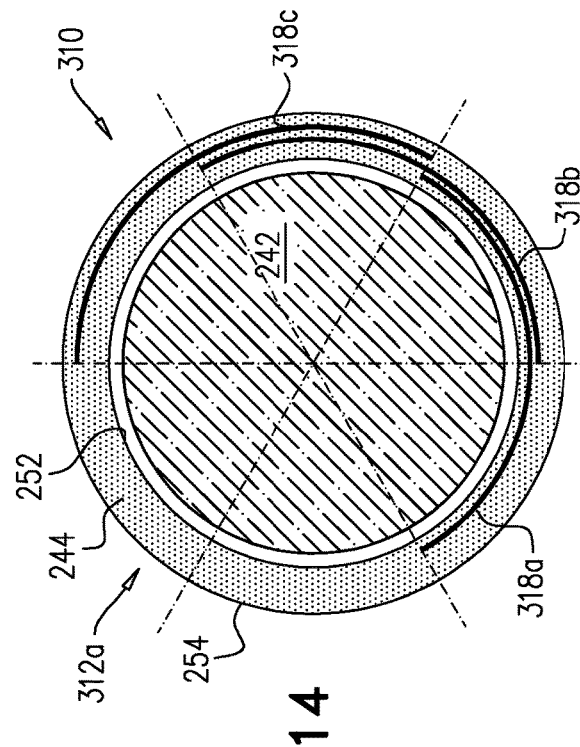

FIGS. 13 and 14 show systems 300 and 310, respectively, each comprising three planar antennas (308a, 308b and 308c; and 318a, 318b and 318c, respectively) that are rotationally offset with respect to each other by 60 degrees. Planar antennas 308a, 308b and 308c of system 300 each span 180 degrees around circumferential wall defined by first face 252 of cuff body 244, and planar antennas 318a, 318b and 318c of system 310 each span 120 degrees around the circumferential wall. It is to be noted that any line that passes through the transverse cross-sectional center of system 300 passes through exactly three antennas, and any line that passes through the transverse cross-sectional center of system 310 passes through exactly two antennas.

It is to be further noted that systems 270, 300 and 310 each define an arc region that does not comprise any portions of an antenna (arc region 272b of system 270, an arc region 302a of system 300, and an arc region 312a of system 310). It is hypothesized that such regions advantageously facilitate cuff body 244 being openable and/or being provided in an open state (e.g., for subsequent wrapping around nerve 242). For example, although not shown in the figures, cuff body 244 may have a discontinuity at such a region.

Figure 15:
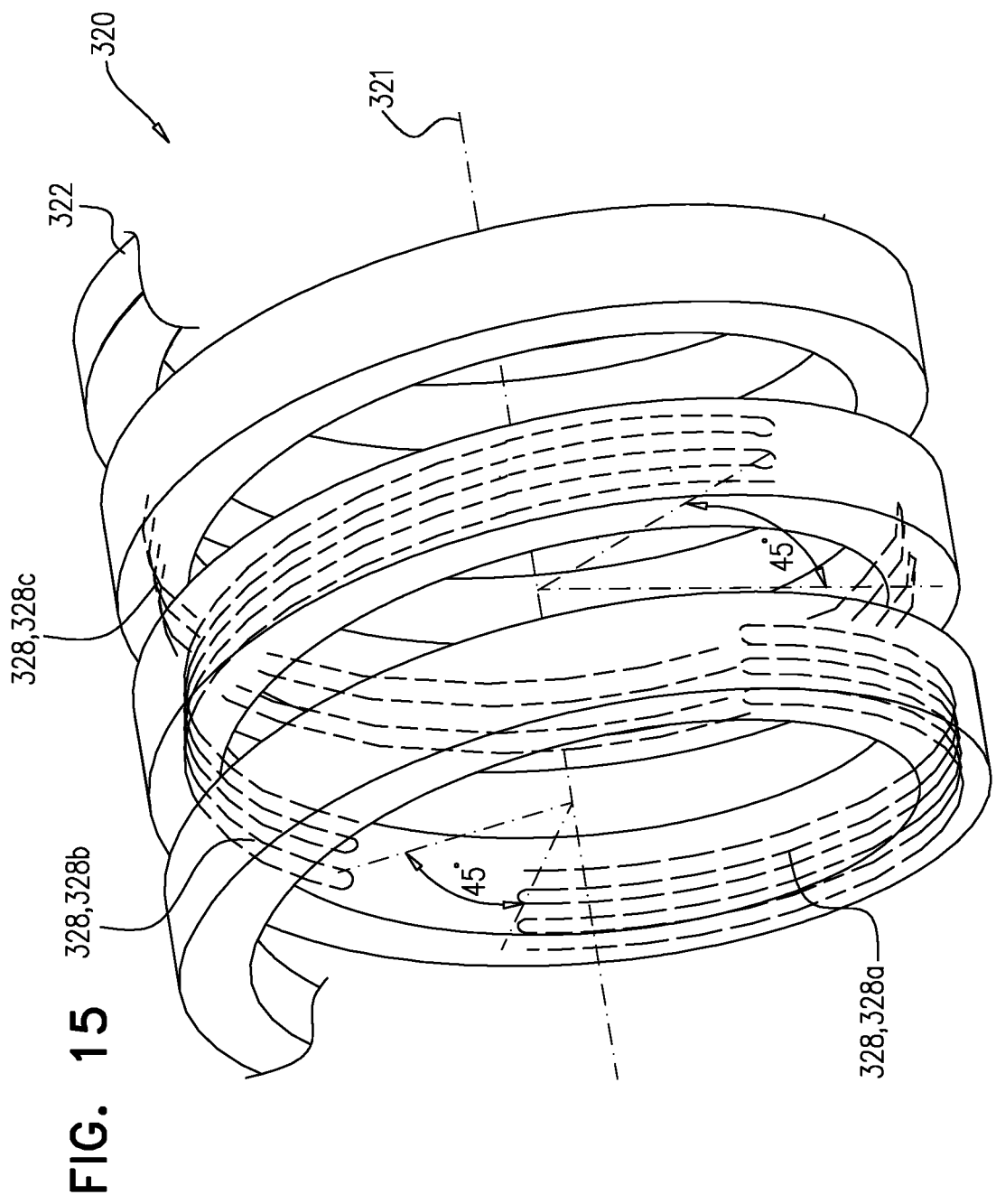
FIG. 15 is a schematic illustration of a helical element comprising a helical body and a plurality of planar antennas, in accordance with some applications of the invention.

Reference is made to FIG. 15, which is a schematic illustration of a helical element 320 comprising a helical body 322 and a plurality of planar antennas 328, in accordance with some applications of the invention. Typically, helical body 322 comprises a helical cuff body, configured to be wrapped around a nerve of a subject. Helical element 320 has a central longitudinal axis 321, around which helical body 322 forms a circumferential wall that typically spans at least once around axis 321. It is to be noted that helical body 322 thereby forms a 360-degree circumferential wall around axis 321, albeit disposed along axis 321 according to the pitch of the helix. Planar antennas 328 are typically disposed within the material of helical body 322. Each planar antenna 328 spans less than 360 degrees around the circumferential wall formed by body 322 (e.g., spans less than one complete turn of the helix). Each planar antenna 328 is typically disposed such that a longest length of the antenna is generally parallel with the helix of helical body 322 (e.g., is shaped to define an incomplete turn of a helix). Planar antennas 328 are disposed progressively along the helix, such that together the antennas form a broken helix within, and parallel to, the helix of helical body 322. Typically, each planar antenna 328 spans no more than 180 degrees around the circumferential wall formed by body 322.

For some applications, and as shown in FIG. 15, helical element 320 comprises three planar antennas 328a, 328b, and 328c, each of the planar antennas spanning 180 degrees around the circumferential wall formed by body 322 (e.g., spans half a complete turn of the helix). Planar antenna 238b is rotationally offset by 225 degrees with respect to planar antenna 328a (e.g., antenna 238b is offset by ⅝ of a turn of the helix with respect to antenna 328a). That is, there is a 45 degree gap around the circumferential wall defined by body 322, between planar antennas 328a and 328b (e.g., there is a ⅛ turn of the helix between antennas 328a and 328b). Planar antenna 328c is rotationally offset with respect to planar antenna 328b to the same degree as planar antenna 328b is rotationally offset with respect to planar antenna 328a. It is to be noted that, viewed from an end of helical element 320, planar antennas 328a, 328b, and 328c have a similar arrangement to planar antennas 288a, 288b, and 288c of system 280 (e.g., the arrangement of antennas 288a, 288b, and 288c may be "projected" onto a helical element). Similarly, any of the antenna arrangements described with reference to FIGS. 8A-14 may be projected onto a helical element.

Reference is again made to FIGS. 11, 12, and 15. It is to be noted that, for some applications, such as those described with reference to FIGS. 11, 12, and 15, each of a plurality of planar antennas spans less than 360 degrees (e.g., no more than 180 degrees) around the longitudinal axis of the cuff and/or helical body, but that all together, the plurality of planar antennas typically spans at least 360 degrees around the longitudinal axis (i.e., at least one of the planar antennas is disposed in each rotational position around the longitudinal axis).

Reference is again made to FIGS. 10-14. It is to be noted that, for some applications in which a cuff body comprises a plurality of overlapping planar antennas, a sum of the areas spanned by the plurality of planar antennas is greater than the area of the cuff body (e.g., the area of a face thereof).

Figures 16, 17, 18:
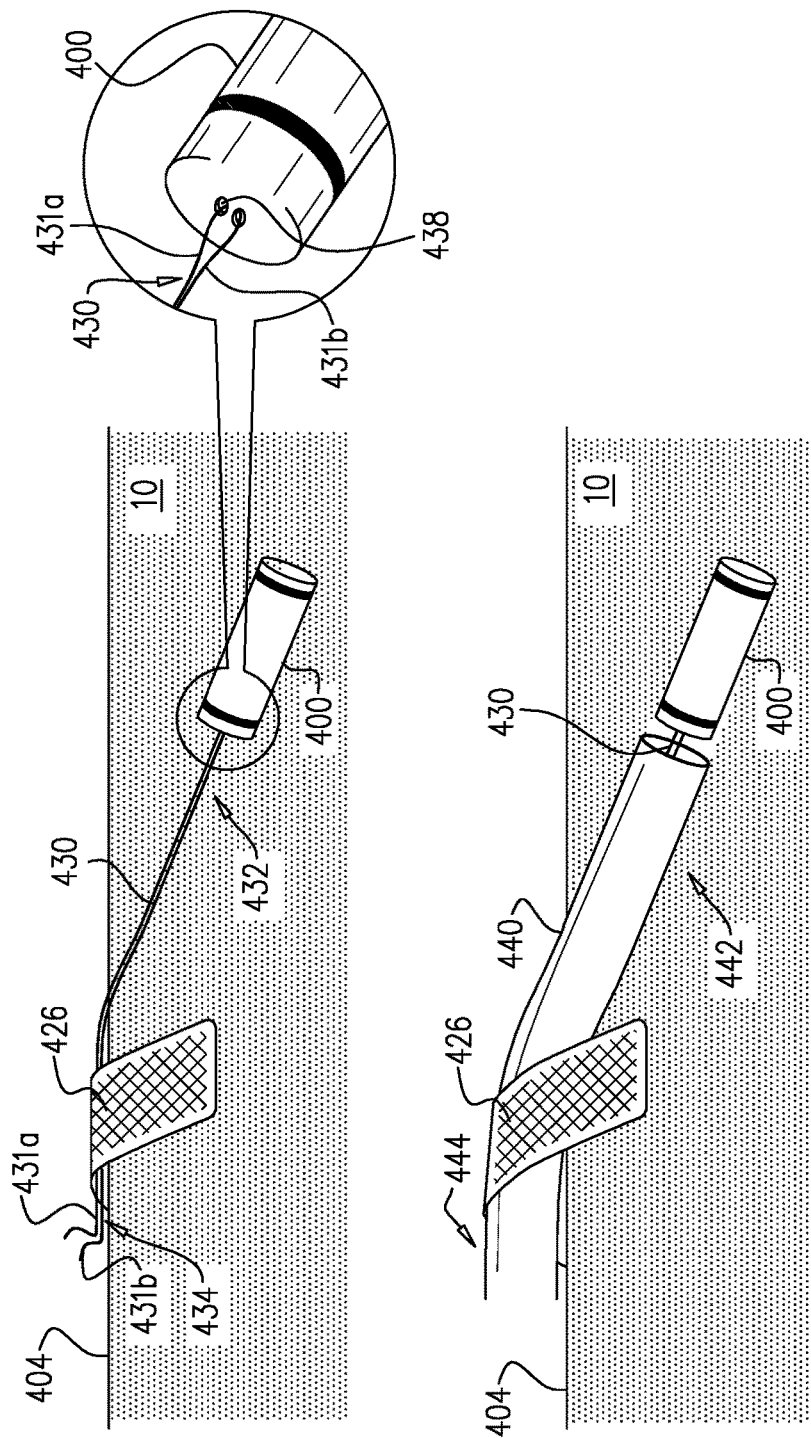
FIGS. 16-18 are schematic illustrations of systems comprising an implant, and at least one longitudinal member having a distal portion configured to be implanted with the implant, and a proximal portion configured to remain outside of the subject, in accordance with some applications of the invention.

Reference is made to FIGS. 16-18, which are schematic illustrations of systems comprising an implant 400, and at least one longitudinal member having a distal portion configured to be implanted with the implant, and a proximal portion configured to remain outside of the subject, in accordance with some applications of the invention. For some applications, implant 400 comprises another implant described herein (e.g., implant 22, implant 52, implant 70, implant 92, implant 170, implant 180 or implant 206).

FIG. 16 shows a longitudinal member 420, reversibly couplable to implant 400 via a locking mechanism 428, which is actuatable from outside of the subject. When implant 400 is percutaneously delivered (e.g., injected) into tissue 10 of the subject, a distal portion 422 of longitudinal member 420 that is coupled to the implant remains coupled to the implant, such that portion 422 is also disposed within the tissue of the subject (e.g., becomes implanted). A proximal portion 424 of longitudinal member 420 remains outside the body of the subject, and is typically secured to a skin surface 404 of the subject (e.g., using tape 426). Typically, longitudinal member 420 is configured to remain in this state for a period of at least 1 day. During this period, longitudinal member 420 may be used to move the implant, e.g., to adjust a position and/or orientation of the implant within tissue 10, and/or to withdraw the implant from the tissue. Longitudinal member 420 is configured to be decoupled from implant 400 by actuating locking mechanism 428, e.g., if it is desirable that implant 400 remain in its position (e.g., permanently). Longitudinal member 420 may be flexible or rigid, and may be shaped as a wire, a rod, a strip, a tube, or any other suitable shape.

FIG. 17 shows a longitudinal member 430, reversibly coupled to implant 400. Longitudinal member 430 is coupled to implant 400 by being looped through an eyelet 438 defined by implant 400, such that two generally parallel domains 431*a*, 431*b* of the longitudinal member are defined. When implant 400 is percutaneously delivered (e.g., injected) into tissue 10 of the subject, a distal portion 432 of longitudinal member 430 that is coupled to the implant remains coupled to the implant, such that portion 432 is also disposed within the tissue of the subject (e.g., becomes implanted). A proximal portion 434 of longitudinal member 430 remains outside the body of the subject, and is typically secured to skin surface 404 of the subject (e.g., using tape 426). Typically, longitudinal member 430 is configured to remain in this state for a period of at least 1 day. Subsequent to implantation of implant 400, longitudinal member 430 may be used to move the implant, e.g., to adjust a position and/or orientation of the implant within tissue 10, and/or to withdraw the implant from the tissue. Longitudinal member 430 is configured to be decoupled from implant 400 by being unthreaded from eyelet 438, e.g., by one of the domains (e.g., domain 431*a*) being pulled, thereby pulling the other one of the domains (e.g., domain 431*b*) through and out of the eyelet. Longitudinal member 430 is typically flexible, and may be shaped as a wire, a strip, or any other suitable shape. For some applications, longitudinal member 430 comprises suture.

For some applications, implant 400 is delivered (e.g., injected) through a tubular longitudinal member 440, and the tubular longitudinal member remains partially implanted subsequent to delivery of the implant (FIG. 18). For some applications, tubular longitudinal member 440 comprises implant-storage member 24, described hereinabove. For some applications, tubular longitudinal member 440 comprises implant-storage member 60, described hereinabove. For some applications, tubular longitudinal member 440 comprises implant-storage member 100 and/or distal portion 98 of delivery tool 94, described hereinabove. For some applications, tubular longitudinal member 440 comprises delivery tube 152, described hereinabove. Following delivery of implant 400 to tissue 10, a distal portion 442 of tubular longitudinal member 440 remains disposed within the tissue, such as slightly proximal to the implant (e.g., distal portion 442 becomes implanted). A proximal portion 444 of tubular longitudinal member 440 remains outside the body of the subject, and is typically secured to a skin surface of the subject (e.g., using tape 426). Typically, tubular longitudinal member 440 is configured to remain in this state for a period of at least 1 day. Subsequent to implantation of implant 400, tubular longitudinal member 440 may be used to access the implant, e.g., to facilitate adjusting a position and/or orientation of the implant within tissue 10, and/or to withdraw the implant from the tissue (e.g., via the tubular longitudinal member). Although FIG. 18 shows tubular longitudinal member 440 being used in combination with longitudinal member 430, it is to be noted that tubular longitudinal member 440 may alternatively be used alone, or in combination with longitudinal member 420.

Reference is again made to FIGS. 16-18. Typically, longitudinal member 420, longitudinal member 430, and tubular longitudinal member 440 are at least in part flexible, so as to facilitate placement of the proximal portion thereof against skin surface 404 (and securing thereto).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
using a tube, advancing an implant that includes an electrode to a nerve of a subject, such that the tube and the implant are arranged at a nonzero angle with respect to a skin surface of the subject;
while the implant is not parallel to the skin surface of the subject, passing the implant distally from an opening of the tube, in a vicinity of a portion of the nerve; and
aligning a longitudinal axis of the implant to become generally parallel with the skin surface by proximally withdrawing the tube from the subject.

2. The method according to claim 1, further comprising, while proximally withdrawing the tube from the subject, using a delivery manipulator to hold the implant still with respect to the portion of the nerve.

3. The method according to claim 1, wherein the nerve is a tibial nerve of the subject.

4. The method according to claim 1, wherein the nonzero angle is greater than 30 degrees.

5. The method according to claim 1, wherein the nonzero angle is less than 45 degrees.

6. The method according to claim 5, wherein the nonzero angle is greater than 30 degrees.

7. The method according to claim 1, wherein advancing the implant comprises deforming the portion of the nerve from an original state to a deformed state, and wherein aligning the longitudinal axis of the implant comprises allowing the portion of the nerve to return to the original state by removing the tube from the subject.

8. The method according to claim 7, wherein:
   deforming the portion of the nerve comprises bringing a longitudinal axis of the portion of the nerve into alignment with the longitudinal axis of the tube; and
   allowing the portion of the nerve to return to the original state comprises allowing the portion of the nerve to return to the original state, while keeping the implant in a generally constant angular disposition with respect to the portion of the nerve.

9. The method according to claim 8, wherein allowing the portion of the nerve to return to the original state comprises allowing the portion of the nerve to return to the original state, while keeping the longitudinal axis of the implant generally parallel to the portion of the nerve.

10. The method according to claim 8, wherein:
    the implant includes at least two electrodes, and
    allowing the portion of the nerve to return to the original state comprises allowing the portion of the nerve to return to the original state, such that each of the electrodes is positioned at the same distance from the nerve.

* * * * *